US007238764B2

(12) United States Patent
De Boer et al.

(10) Patent No.: US 7,238,764 B2
(45) Date of Patent: Jul. 3, 2007

(54) PROCESS FOR THE CO-OLIGOMERISATION OF ETHYLENE AND ALPHA OLEFINS

(75) Inventors: Eric Johannes Maria De Boer, Amsterdam (NL); Hendrikus Hyacinthus Deuling, Amsterdam (NL); Harry Van Der Heijden, Amsterdam (NL); Quoc An On, Amsterdam (NL); Aart Bartus Van Oort, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 81 days.

(21) Appl. No.: 10/739,715

(22) Filed: Dec. 18, 2003

(65) Prior Publication Data
US 2005/0059786 A1  Mar. 17, 2005

Related U.S. Application Data

(62) Division of application No. 09/964,714, filed on Sep. 27, 2001, now Pat. No. 7,037,988.

(30) Foreign Application Priority Data
Oct. 3, 2000  (EP) ................................ 00308728
Aug. 1, 2001  (EP) ................................ 01306601

(51) Int. Cl.
C08F 110/04 (2006.01)
C08F 110/14 (2006.01)
(52) U.S. Cl. ..................... 526/348; 526/348.6
(58) Field of Classification Search ............... 526/348, 526/348.6
See application file for complete search history.

(56) References Cited

U.S. PATENT DOCUMENTS

| | | | |
|---|---|---|---|
| 4,728,583 A | 3/1988 | Yamazaki et al. ........... 428/690 |
| 4,822,911 A * | 4/1989 | Fried ........................... 560/205 |
| 4,912,333 A | 3/1990 | Roberts et al. .......... 250/487.1 |
| 4,944,026 A | 7/1990 | Arakawa et al. ......... 250/484.1 |
| 5,151,604 A | 9/1992 | Kohda et al. ............. 250/484.1 |
| 5,318,935 A | 6/1994 | Canich et al. ............... 502/117 |
| 5,726,115 A | 3/1998 | Horton et al. ............... 502/152 |
| 5,830,629 A | 11/1998 | Vizard et al. ................ 430/529 |
| 5,852,145 A | 12/1998 | McLain et al. .............. 526/133 |
| 5,888,647 A | 3/1999 | Yamane ....................... 428/338 |
| 5,905,014 A | 5/1999 | Van de Bergh .............. 430/139 |
| 5,955,555 A | 9/1999 | Bennett ....................... 526/133 |
| 6,002,034 A | 12/1999 | McLain et al. ................ 556/34 |
| 6,063,881 A | 5/2000 | Bennett ....................... 526/161 |
| 6,103,946 A | 8/2000 | Brookhart, III et al. .... 585/523 |
| 6,150,482 A | 11/2000 | Brookhart et al. .......... 526/161 |
| 6,214,761 B1 | 4/2001 | Bennett ....................... 502/117 |
| 6,232,259 B1 | 5/2001 | Ittel et al. .................... 502/155 |
| 6,265,500 B1 | 7/2001 | Debras ......................... 526/65 |
| 6,310,153 B2 | 10/2001 | Ittel et al. .................... 526/172 |
| 6,395,668 B1 | 5/2002 | van Baar et al. ........... 502/123 |
| 6,407,188 B1 | 6/2002 | Guan et al. .................. 526/113 |
| 6,414,098 B1 | 7/2002 | Engehausen et al. ....... 526/161 |
| 6,417,305 B2 | 7/2002 | Bennett ....................... 526/161 |
| 6,417,364 B1 | 7/2002 | Lenges ......................... 546/12 |
| 6,423,848 B2 | 7/2002 | Bennett ....................... 546/329 |
| 6,432,862 B1 | 8/2002 | Bennett ....................... 502/117 |
| 6,441,117 B1 | 8/2002 | Cameron ..................... 525/352 |
| 6,451,939 B1 | 9/2002 | Britovsek et al. ........... 525/161 |
| 6,455,660 B1 | 9/2002 | Clutton et al. .............. 526/352 |
| 6,458,739 B1 | 10/2002 | Kimberley et al. ......... 502/155 |
| 6,458,905 B1 | 10/2002 | Schmidt et al. ............. 526/172 |
| 6,461,994 B1 | 10/2002 | Gibson et al. .............. 502/155 |
| 6,462,152 B1 | 10/2002 | Berardi et al. ................ 526/75 |
| 6,462,155 B1 | 10/2002 | Okuda ......................... 526/161 |
| 6,465,386 B1 | 10/2002 | Maddox et al. ............. 502/155 |
| 6,472,341 B1 | 10/2002 | Kimberley et al. ......... 502/155 |
| 6,479,601 B1 | 11/2002 | Kerns et al. ................. 526/161 |
| 6,489,497 B1 | 12/2002 | Brookhart, III et al. .... 556/138 |
| 6,521,329 B2 | 2/2003 | Aylward et al. ............. 428/212 |
| 6,534,691 B2 | 3/2003 | Culver et al. ................ 585/527 |
| 6,545,108 B1 | 4/2003 | Moody et al. ............... 526/161 |
| 6,548,672 B1 | 4/2003 | Gibson et al. ................ 546/12 |
| 6,555,723 B2 | 4/2003 | Schiffino ..................... 585/521 |
| 6,559,091 B1 | 5/2003 | Moody et al. ............... 502/167 |
| 6,559,252 B1 | 5/2003 | Horton et al. ............... 526/160 |
| 6,583,237 B1 | 6/2003 | Imuta et al. ................... 526/89 |
| 6,605,677 B2 | 8/2003 | Lavoie et al. ................ 526/161 |
| 6,677,267 B2 | 1/2004 | Berardi et al. ............... 502/155 |
| 6,683,141 B1 | 1/2004 | Gibson et al. .............. 526/161 |
| 6,683,187 B2 | 1/2004 | De Boer et al. ............ 546/345 |
| 6,706,891 B2 | 3/2004 | Ponasik ....................... 548/523 |
| 6,710,006 B2 | 3/2004 | De Boer et al. ............ 502/155 |
| 6,740,715 B2 | 5/2004 | Brookhart, III et al. .... 526/161 |
| 6,825,297 B1 | 11/2004 | Devore et al. .............. 526/172 |
| 6,838,540 B2 | 1/2005 | Mitani et al. ................ 526/348 |
| 2001/0000519 A1 | 4/2001 | Bennett ......................... 526/90 |
| 2001/0016634 A1 | 8/2001 | Ittel et al. .................... 526/172 |

(Continued)

FOREIGN PATENT DOCUMENTS

EP    0308728    3/1989

(Continued)

OTHER PUBLICATIONS

Office Action of Nov. 29, 2004 in (U.S. Appl. No. 10 208,535, filed Jul. 30, 2002).

(Continued)

Primary Examiner—Robert D. Harlan

(57) ABSTRACT

A process for production of higher linear alpha olefins and/or alkyl-branched alpha olefins, which comprises the co-oligomerisation of one or more alpha olefins with ethylene in the presence of a metal catalyst system employing one or more bis-aryliminepyridine $MX_q$ complexes and/or one or more [bis-aryliminepyridine $MY_p.L_b^+$][$NC^-$]$_q$ complexes; and said process is carried out at an ethylene pressure of less than 2.5 MPa.

24 Claims, 3 Drawing Sheets

U.S. PATENT DOCUMENTS

| | | | |
|---|---|---|---|
| 2002/0013431 A1 | 1/2002 | Bennett | 526/90 |
| 2002/0016425 A1 | 2/2002 | De Boer et al. | 526/172 |
| 2002/0016521 A1 | 2/2002 | Culver et al. | 585/527 |
| 2002/0019575 A1 | 2/2002 | Schiffino | 585/520 |
| 2002/0028941 A1 | 3/2002 | De Boer et al. | 546/167 |
| 2002/0035031 A1 | 3/2002 | Berardi et al. | 502/171 |
| 2002/0128409 A1 | 9/2002 | De Boer et al. | 526/172 |
| 2003/0036615 A1 | 2/2003 | Brookhart, III et al. | 526/161 |
| 2003/0045752 A1 | 3/2003 | De Boer et al. | 562/545 |
| 2003/0050494 A1 | 3/2003 | Brookhart, III et al. | 556/138 |
| 2003/0119921 A1 | 6/2003 | De Boer et al. | 518/715 |
| 2003/0125195 A1 | 7/2003 | Britovsek et al. | 502/117 |
| 2003/0144514 A1 | 7/2003 | De Boer et al. | 546/12 |
| 2003/0195110 A1 | 10/2003 | Moody et al. | 502/150 |
| 2003/0225228 A1 | 12/2003 | Moody et al. | 526/172 |
| 2004/0116758 A1 | 6/2004 | De Boer et al. | 585/521 |
| 2005/0014983 A1 | 1/2005 | De Boer et al. | 585/511 |
| 2005/0159601 A1 | 7/2005 | De Boer et al. | 546/2 |

FOREIGN PATENT DOCUMENTS

| | | |
|---|---|---|
| EP | 1125928 A1 | 8/2001 |
| EP | 1125987 A2 | 8/2001 |
| EP | 1127987 A1 | 8/2001 |
| EP | 0927201 B1 | 4/2004 |
| JP | 04325504 | 11/1992 |
| SU | 418462 | 3/1974 |
| WO | WO 92/12162 | 7/1992 |
| WO | WO 96/27439 | 9/1996 |
| WO | WO 98/27124 | 6/1998 |
| WO | WO 99/02472 | 1/1999 |
| WO | WO 99/51550 | 1/1999 |
| WO | WO 99/12981 | 3/1999 |
| WO | WO 99/51550 | 10/1999 |
| WO | 99/62967 | 12/1999 |
| WO | WO 99/62967 * | 12/1999 |
| WO | WO 00/08034 | 2/2000 |
| WO | WO 00/15646 | 3/2000 |
| WO | WO 00/20427 | 4/2000 |
| WO | WO 00/50470 | 8/2000 |
| WO | WO 01/36379 A1 | 5/2001 |
| WO | WO 02/28805 A2 | 4/2002 |

OTHER PUBLICATIONS

Olefin Polymerization with [{bis(imino)pyridyl}Co$^{II}$Cl$_2$]: Generation of the Active Species Involves Co$^{I}$**, by T. Martijn Kooistra et al., Angewandte Chemie. International Edition, Wiley-VCH, Weinheim, DE, vol. 40, No. 24, Dec. 17, 2001, pp. 4719-4722.

"The Nature of the Active Species in Bis(imino)pyridyl Cobalt Ethylene Polymerisation Catalysts," by Vernon C. Gibson, et al., Chemical Communications-Chemcom, Royal Society of Chemistry, GB, No. 21, 2001, pp. 2252-2253.

"Late Metal Catalysts for Ethylene Home- and Copolymerization," by Steven D. Ittel et al., Chemical Reviews, American Chemical Society, Easton, US, vol. 100, No. 4, 2000, pp. 1169-1203.

"Novel Olefin Polymerization Catalysts Based on Iron and Cobalt," by George J. P. Britovsek et al., Chemical Communications-Chemcom, Roayl Society of Chemistry, GB, No. 7, 1998, pp. 849-850.

U.S. Appl. No. 09/775,128, filed Feb. 1, 2001, DeBoer et al.

"Oligomerization of Ethylene to Higher α-Olefins in Applied Homogeneous Catalysis With Organometallic Compounds," by D. Vogt, Ed. B. Cornilis, W. A. Herrmann, vol. 1, Ch. 2.3.1.3, VCH (1996) pp. 245-258.

"Iron-Based Catalysts With Exceptionally High Activities and Selectivities for Oligomerization of Ethylene to Linear α-Olefins," B. L. Small and M. Brookhard disclosed in *J. Am. Chem. Soc.* 1998, 120, pp. 7143-7144.

"Oligomerisation of Ethylene by Bis(Imino)Pyridyliron and—Cobalt Complexes," by G. J. P. Britovsek, S. Mastroianni, G. A. Solan, S. P. D. Baugh, C. Redshaw, V. C. Gibson, A. J. P. White, D. J. Williams, and M. R. J. Elsegood, as disclosed in *Chem. Eur. J. 2000*, 6, pp. 2221-2231.

George J. P. Britovsek et al., "Iron-Catalyzed Polyethylene Chain Growth on Zinc: Linear α-Olefins with a Poisson Distribution," Angew. Chem. Int. Ed. 2002, 41, No. 3, pp. 489-491.

Francis Lions et al., "Tridentate Chelate Compounds. I," J. Am. Chem. Soc. (1957), vol. 79, pp. 2733-2738.

Paul E. Figgins et al., "Complexes of Iron (II), Cobalt (II) and Nickel (II) with Biacetyl-bis-methylimine, 2-Pyridinal-methylimine and 2,6-Pyridindial-bis-methylimine," J. Am. Chem. Soc. (1960) vol. 82, pp. 820-824.

"Novel, Highly Active Iron and Cobalt Catalysts for Olefin Polymerization," by Allison M. A. Bennett, Chemtech, Jul. 1999, pp. 24-28.

"Polymerization of Propylene by a New Generation of Iron Catalysts: Mechanisms of Chain Initiation, Propagation, and Termination," by Brooke L. Small and Maurice Brookhart, Macromolecules, vol. 32, No. 7, 1999, pp. 2120-2130.

U.S. Appl. No. 11/080,170, filed Mar. 15, 2005, De Boer et al.

"Metal-Ion-Directed Synthesis of Homo- and Heteronuclear Dimetallic Schiff Base Podates," by W. Radecka-Paryzek, M. T. Kaczmarek, and E. Luks, Polish J. Chem., 75, (2001) pp. 35-42.

"1,1-Diisocyanoferrocene and a Convenient Synthesis of Ferrocenylamine," by Daan van Leusen and Bart Hessen, Organometallics, 2001, pp. 224-226.

U.S. Appl. No. 09/964,714, filed Sep. 27, 2001, De Boer et al.

U.S. Appl. No. 10/668,592, filed Sep. 23, 2003, De Boer et al.

U.S. Appl. No. 10/208,535, filed Jul. 30, 2002, De Boer et al.

U.S. Appl. No. 10/320,213, filed Dec. 16, 2002, De Boer et al.

D. Van Leusen and B. Hessen, Organometallics, 2001, 20, pp. 224/226.

Chemical Abstracts, vol. 134, Columbus, Ohio, US; Abstract No. 231149, Radecka-Paryzek, W. et al., "Metal-Ion-Directed Synthesis of Homo- and Heteronuclear Dimetallic Schiff Base Podates," Pol. J. Chem. 2001, 75(1), pp. 35-42.

* cited by examiner

PROCESS FOR THE CO-OLIGOMERISATION OF ETHYLENE AND ALPHA OLEFINS

This is a division of application Ser. No. 09/964,714 filed Sep. 27, 2001, now U.S. Pat. No. 7,037,988 the entire disclosure of which is hereby incorporated by reference.

FIELD OF THE INVENTION

The present invention relates to a process for the co-oligomerisation of ethylene and alpha olefins and to product compositions produced therein.

BACKGROUND OF THE INVENTION

Various processes are known for the production of higher linear alpha olefins (for example D. Vogt, *Oligomerisation of ethylene to higher α-olefins* in *Applied Homogeneous Catalysis with Organometallic Compounds* Ed. B. Cornils, W. A. Herrmann Vol. 1, Ch. 2.3.1.3, page 245, VCH 1996).

These commercial processes afford either a Poisson or Schulz-Flory oligomer product distribution. In order to obtain a Poisson distribution, no chain termination must take place during oligomerisation. However, in contrast, in a Schulz-Flory process, chain termination does occur and is independent of chain length. The Ni-catalysed ethylene oligomerisation step of the Shell Higher Olefins Process (SHOP) is a typical example of a Schulz-Flory process.

In a Schulz-Flory process, a wide range of oligomers are typically made in which the fraction of each olefin can be determined by calculation on the basis of the so-called K-factor. The K-factor, which is indicative of the relative proportions of the product olefins, is the molar ratio of $[C_{n+2}]/[C_n]$ calculated from the slope of the graph of log $[C_n$ mol %] versus n, where n is the number of carbon atoms in a particular product olefin. The K-factor is by definition the same for each n. By ligand variation and adjustment of reaction parameters, the K-factor can be adjusted to higher or lower values. In this way, the process can be operated to produce a product slate with an optimised economic benefit.

In WO-A-99/02472, there are disclosed novel iron-based ethylene oligomerisation catalysts that show high activity and high selectivity towards linear alpha olefins. The catalysts are based on iron complexes of a selected 2,6-pyridinedicarboxaldehyde bisimine or a selected 2,6-diacylpyridine bisimine.

In the present invention the term "bis-(aryliminoalkyl) pyridine", or in short, "bis-aryliminepyridine" is used to describe both classes of ligands.

In a co-pending U.S. patent application Ser. No. 09/775,128 such systems are further improved, in particular with respect to the oligomer product distribution.

The bis-aryliminepyridine-FeCl$_2$ based catalysts have been shown to be highly reactive towards ethylene but the reactivity towards other olefins such as propylene or higher alpha olefins has been found to be orders of magnitude lower.

B. L. Small and M. Brookhart disclosed in J. Am. Chem. Soc. 1998, 120, 7143-7144, that the oligomerisation of ethylene at a pressure of 400 psig (2.76 MPa) in the presence of a 50:50 volume ratio of 1-pentene to toluene as solvent and a bis-arylimine pyridine-FeCl$_2$ based catalyst gave only ca. 3 mol. % of odd carbon number oligomers, thereby demonstrating the very high selectivity of such a catalyst for insertion of ethylene relative to alpha olefins.

Further experiments therein with a different bis-aryliminepyridine-FeCl$_2$ catalyst showed even greater selectivity towards insertion of ethylene relative to the insertion of alpha olefins, with only traces (<1%) of odd oligomers produced.

The high selectivity of these catalysts towards ethylene was confirmed by the studies of V. C. Gibson et al., as disclosed in Chem. Eur. J. 2000, 6, 2221-2231.

Therefore, not surprisingly, the application of such catalyst systems has focused on products and processes with ethylene as feedstock and with preferentially no or little branching in products, for example, production of linear alpha olefins.

SUMMARY OF THE INVENTION

A process for production of higher linear alpha olefins and/or alkyl-branched alpha olefins is provided, comprising the co-oligomerisation of one or more alpha olefins with ethylene in the presence of a metal catalyst system employing one or more bis-aryliminepyridine $MX_a$ complexes and/or one or more [bis-aryliminepyridine $MY_p.L_b^+$][$NC^-$]$_q$ complexes, said bis-aryliminepyridine complexes comprising a ligand of the formula,

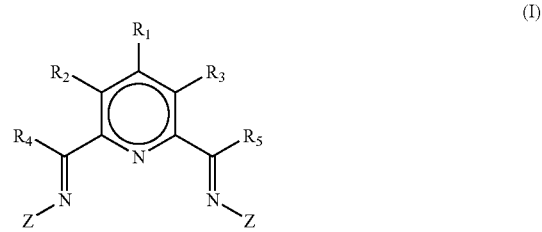

(I)

wherein M is a metal atom selected from Fe or Co; a is 2 or 3; X is halide, optionally substituted hydrocarbyl, alkoxide, amide, or hydride; Y is a ligand which may insert an olefin; NC$^-$ is a non-coordinating anion; p+q is 2 or 3, matching the formal oxidation of said metal atom; L is a neutral Lewis donor molecule; b=0, 1, or 2; $R_1$-$R_5$ are each, independently, hydrogen, optionally substituted hydrocarbyl, an inert functional group, or any two of $R_1$-$R_3$ vicinal to one another taken together may form a ring; each Z, which may be identical or different, is an optionally substituted aromatic hydrocarbon ring; an optionally substituted polyaromatic hydrocarbon moiety; an optionally substituted heterohydrocarbyl moiety; or an optionally substituted aromatic hydrocarbon ring in combination with a metal, said optionally substituted aromatic hydrocarbon ring being π-co-ordinated to the metal; and said process is carried out at an ethylene pressure of less than 2.5 MPa.

DETAILED DESCRIPTION OF THE INVENTION

Figure 1:
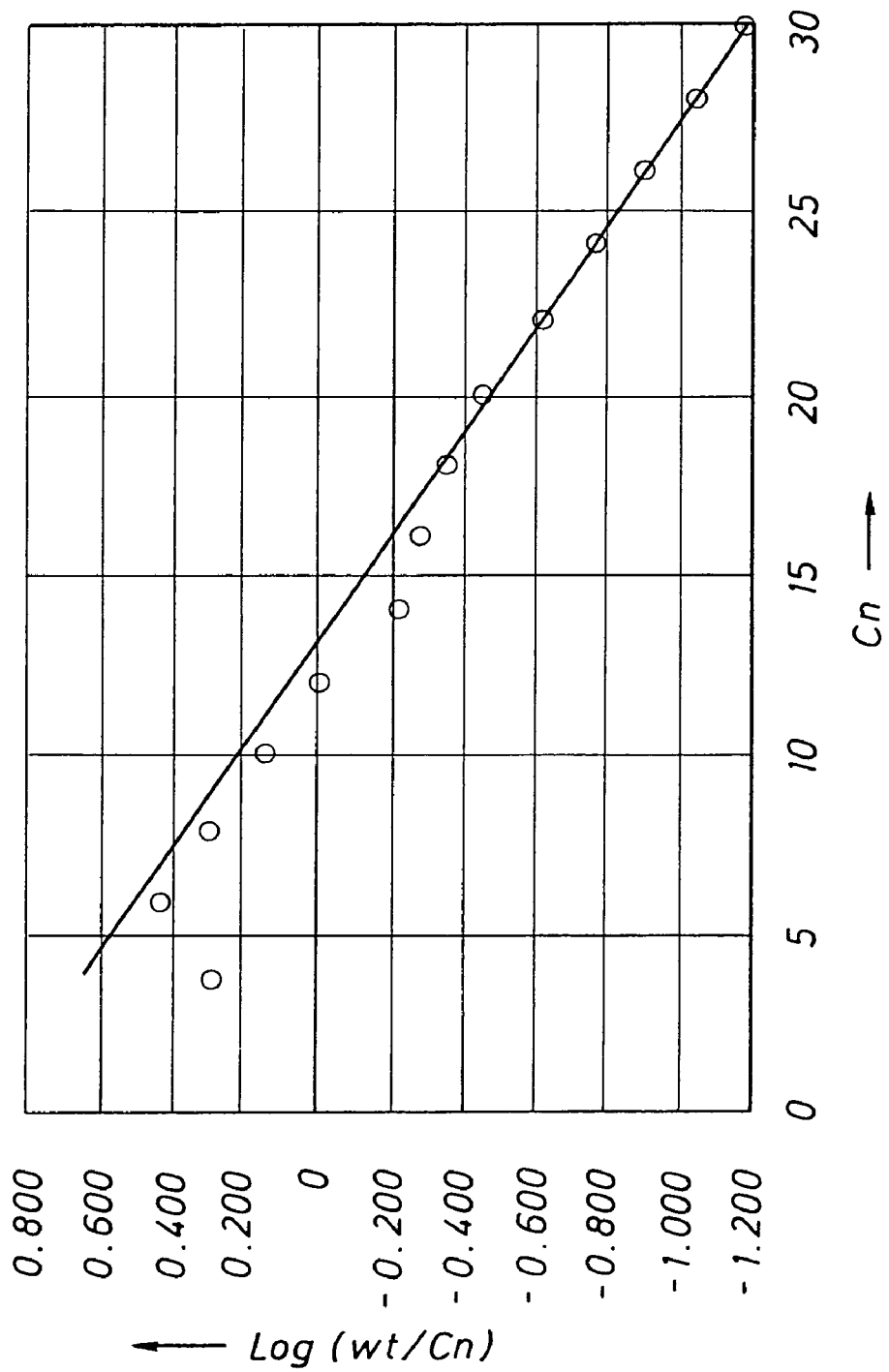
FIG. 1 is a regression analysis of Example 4.

For an oligomerisation process, the basic reaction steps of chain growth and chain termination are balanced in such a way that products with a limited molecular weight are formed, that is to say, the amount of products with high molecular weights is minimal.

In a simplified view, one may consider chain growth to occur by ethylene insertion in a metal-hydrogen bond (for the first monomer affording a metal-ethyl species) and metal-carbon bonds (for the second monomer and more).

It is a general phenomenon that other olefins besides ethylene may participate in reactions with metal-hydrogen or metal-carbon bonds. In particular, mono-substituted alpha olefins are reactive. The outcome of the reaction is influenced by the structures of the active intermediates, the way the alpha olefins react with these, and the way the generated metal-alkyl compounds react further.

In ethylene oligomerisation reactions, the formation of by-products such as branched olefins, 2,2-substituted alpha olefins (vinylidene-type olefins), and internal olefins can be readily explained by these intermediates. It will be evident that in view of the alpha olefin oligomer distribution generated in ethylene oligomerisations, a wide array of by-products may form leading to loss of product quality and waste of valuable ethylene feed. However, catalysts which combine a particular reactivity towards alpha-olefins with ethylene oligomerisation capability would be of great value to generate new technologies for producing alpha olefins from alternative feedstocks or for (mixtures of) alpha olefin products with particular structures designed in order to exhibit desirable properties.

For example, producing 1-hexene, 1-octene, or 1-decene by homologation of 1-butene with ethylene can be envisioned by systems which after chain termination start by "1,2"-insertion of 1-butene in the metal-hydrogen bond (formed after chain termination) but which subsequently do not react extensively with any other olefin but ethylene before termination. In this way, cheaply available refinery 1-butene can be converted to high-valued alpha olefins.

Another interesting possibility is the formation of alkyl-branched alpha olefins with a well-defined branching pattern as a result of catalyst properties and reaction conditions. For example, methyl-branched alpha olefins may be obtained by systems which after chain termination preferentially start with "2,1"-insertion of an olefin into the metal-hydrogen bond and which subsequently do not react extensively with any other olefin than ethylene before termination.

In the present invention by "methyl-branched alpha olefin" is meant an olefin formed by "2,1"-insertion of an alpha olefin formally into the metal-hydrogen bond of the system and which system subsequently does not react extensively with any other olefin than ethylene before termination. This "2,1"-insertion of an olefin into the metal-hydrogen bond may alternatively be explained by chain termination by hydrogen transfer to a co-ordinated olefin providing a metal-(2-alkyl) species as the start for the oligomerisation process. For sake of simplicity the first-mentioned mechanism will be adhered to in the further text.

The formation of $C_8$-$C_{16}$ methyl-branched alpha-olefins is of great economic value as they may serve as feedstock for the alkylation of benzene, and thereby providing starting materials for high-solubility alkylbenzene sulphonate surfactants, and as feedstock for hydroformylation processes yielding high-solubility detergent alcohols and derivatives.

Moreover, if, for example, 1-decene were to be used as the "solvent" for ethylene (co-)oligomerisation, one single process would yield linear 1-alkenes in the $C_4$-$C_{10}$ range as well as linear and/or branched 1-alkenes in the range >$C_{12}$.

Besides specific methyl-branching, products with specific ethyl-branching are of economical interest. Preference for ethyl-branching can be envisaged to be endorsed in catalyst systems in which the chain transfer reaction preferably takes place to ethylene monomer. In the resulting metal-ethyl species, chain growth may occur either by incorporation of additional ethylene or a different olefinic co-monomer.

In the present invention by "ethyl-branched alpha olefin" is meant an olefin formed by "1,2"-insertion of an alpha olefin formally into the metal-ethyl bond of the system and which system subsequently does not react extensively with any other olefin than ethylene before termination.

Ascertaining whether the proposed reactions and formation of the desired molecular structures described above have taken place during ethylene oligomerisation, is thwarted by the fact that the same product may be generated by more than one reaction path.

For example, linear alpha olefins may be formed not only by pure ethylene oligomerisation but also homologation of a smaller "1,2"-inserted alpha olefin with ethylene.

A more detailed insight into products and reaction steps may be obtained from co-oligomerisation experiments in which the co-monomer is an odd-numbered alpha olefin. Ethylene oligomerisations which take place in the presence of odd-numbered alpha olefins will give information on incorporation of olefins in products by comparison and characterisation of odd- and even-numbered products. For example, ethylene oligomerisation in the presence of 1-heptene may afford the usual $C_{2n}$ alpha olefins as well as the linear odd alpha olefins starting from 1-nonene, $C_9$. The ratio of the amounts of odd and even linear olefins provides a measure of the relative reactivities of ethylene and alpha olefins in the first step of the chain growth in experiments.

Important information on (by-)product structures in ethylene oligomerisations may be obtained by performing the reaction in the presence of a large excess of a particular alpha olefin, for example, a co-oligomerisation. This has the effect of simplifying the normally obtained oligomer distribution by a singular olefin of the same reactivity. As a result (by-)product formation due to incorporation of produced alpha olefins based on the single co-monomer and yield well-defined structures is now apparent.

These structures are relatively easy to characterise even if present in small amounts by comparison of $^1H$- and $^{13}C$-NMR spectra of samples containing different levels of (by-)products. Characteristic NMR resonances for unsaturated end-groups in alpha-olefins, 2,2-disubstituted alpha olefins (vinylidene type olefins), single methyl and ethyl groups along an aliphatic chain are known in the literature and can be used.

The presence of 2,2-disubstituted alpha olefins can be explained by "1,2"-insertion of an alpha olefin into the metal carbon bond of a growing chain, followed by chain termination (β-H elimination). The occurrence of a distribution of methyl-branched alpha olefins is in line with a chain growth process in which the first step of the reaction involves, a "2,1"-insertion of the co-monomer formally in a metal-hydride affording a metal-(2-alkyl) intermediate which undergoes subsequent ethylene oligomerisations. In a similar fashion, the occurrence of a distribution of ethyl-branched alpha olefins can be explained by assuming that chain termination occurs by hydrogen transfer to a co-ordinated ethylene monomer providing a metal-ethyl species as the start for the oligomerisation process in which the first step is a "1,2"-insertion of an alpha olefin into this metal-ethyl bond, affording a metal-(3-alkyl) intermediate which undergoes subsequent ethylene oligomerisations. Of course, the type of by-products observed should show similar patterns for odd- and even-numbered alpha olefin co-monomer.

It has now been surprisingly found that by tuning reaction conditions, in particular using suitable olefins at appropriate concentrations in an ethylene co-oligomerisation reaction and the specific bis-aryliminepyridine metal catalyst systems used therein, the formation of linear alpha olefins by ethylene-homologation of smaller linear alpha olefins and the formation of alkyl-branched, in particular methyl-branched and/or ethyl-branched, alpha olefins can be greatly enhanced.

By "alkyl-branched alpha olefin" in the present invention is meant preferably "methyl-branched alpha olefin", "ethyl-branched alpha olefin" or a combination thereof.

It will be appreciated that whilst the alkyl-branched alpha olefins of the present invention may be formed by the tentative mechanisms described above, it is not precluded that said olefins may be formed by an alternative reaction mechanism.

The general structure of "alkyl-branched alpha olefins" is given in the formula below,

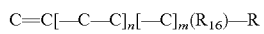

wherein $R_{16}$ =methyl; n=0, 1, 2, etc.; m=1; R=optionally substituted hydrocarbyl, preferably comprising 1 to 30 carbon atoms, or $R_{16}$=ethyl; n=0, 1, 2, etc.; m=0; R=optionally substituted hydrocarbyl, preferably comprising 1 to 30 carbon atoms.

The present invention provides a process for production of higher linear alpha olefins and/or alkyl-branched alpha olefins, which comprises the co-oligomerisation of one or more alpha olefins with ethylene in the presence of a metal catalyst system employing one or more bis-aryliminepyridine $MX_a$ complexes and/or one or more [bis-aryliminepyridine $MY_p.L_b^+$][$NC^-$]$_q$ complexes, said bis-aryliminepyridine complexes comprising a ligand of the formula,

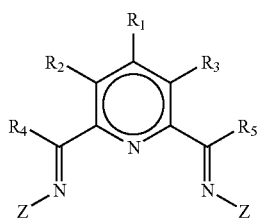

wherein M is a metal atom selected from Fe or Co; a is 2 or 3; X is halide, optionally substituted hydrocarbyl, alkoxide, amide, or hydride; Y is a ligand which may insert an olefin; $NC^-$ is a non-coordinating anion; p+q is 2 or 3, matching the formal oxidation of said metal atom; L is a neutral Lewis donor molecule; b=0, 1, or 2; $R_1$-$R_5$ are each, independently, hydrogen, optionally substituted hydrocarbyl, an inert functional group, or any two of $R_1$-$R_3$ vicinal to one another taken together may form a ring; each Z, which may be identical or different, is an optionally substituted aromatic hydrocarbon ring; an optionally substituted polyaromatic hydrocarbon moiety; an optionally substituted heterohydrocarbyl moiety; or an optionally substituted aromatic hydrocarbon ring in combination with a metal, said optionally substituted aromatic hydrocarbon ring being π-co-ordinated to the metal;

and said process is carried out at an ethylene pressure of less than 2.5 MPa.

In a preferred embodiment of the present invention, there is provided a process for production of higher linear alpha olefins and/or alkyl-branched alpha olefins, which comprises the co-oligomerisation of one or more alpha olefins with ethylene in the presence of a metal catalyst system employing one or more bis-aryliminepyridine $MX_a$ complexes and/or one or more [bis-aryliminepyridine $MY_p.L_b^+$] [$NC^{31}$]$_q$ complexes, said bis-aryliminepyridine complexes comprising a ligand of the formula,

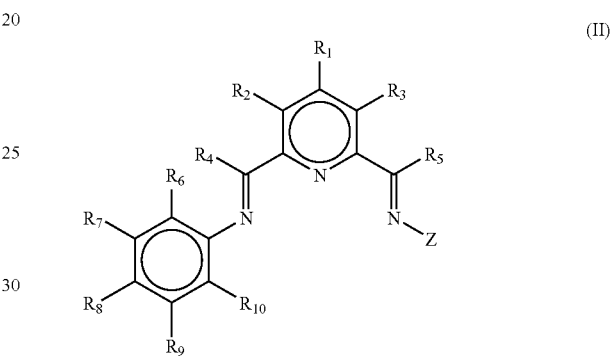

wherein M is a metal atom selected from Fe or Co; a is 2 or 3; X is halide, optionally substituted hydrocarbyl, alkoxide, amide, or hydride; Y is a ligand which may insert an olefin; $NC^-$ is a non-coordinating anion; p+q is 2 or 3, matching the formal oxidation of said metal atom; L is a neutral Lewis donor molecule; b=0, 1, or 2; $R_1$-$R_{10}$ are each, independently, hydrogen, optionally substituted hydrocarbyl, an inert functional group, or any two of $R_1$-$R_3$, $R_6$-$R_{10}$ vicinal to one another taken together may form a ring; $R_6$ may be taken together with $R_4$ to form a ring; $R_{10}$ may be taken together with $R_4$ to form a ring; Z is an optionally substituted aromatic hydrocarbon ring; an optionally substituted polyaromatic hydrocarbon moiety; an optionally substituted heterohydrocarbyl moiety; or an optionally substituted aromatic hydrocarbon ring in combination with a metal, said optionally substituted aromatic hydrocarbon ring being π-co-ordinated to the metal; and said process is carried out at an ethylene pressure of less than 2.5 MPa.

In a preferred embodiment of the present invention, there is provided a process for production of higher linear alpha olefins and/or alkyl-branched alpha olefins, which comprises the co-oligomerisation of one or more alpha olefins with ethylene in the presence of a metal catalyst system employing one or more bis-aryliminepyridine $MX_a$ complexes and/or one or more [bis-aryliminepyridine $MY_p.L_b^+9$ [$NC$-]$_q$ complexes, said bis-aryliminepyridine complexes comprising a ligand of the formula,

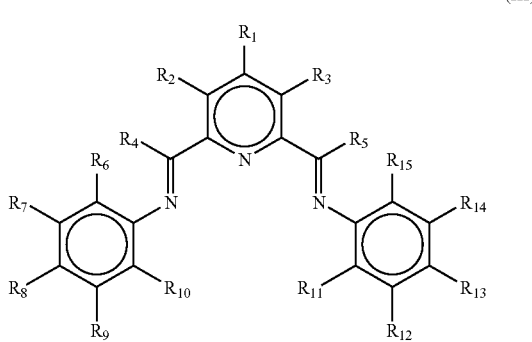

(III)

wherein M is a metal atom selected from Fe or Co; a is 2 or 3; X is halide, optionally substituted hydrocarbyl, alkoxide, amide, or hydride; Y is a ligand which may insert an olefin; $NC^-$ is a non-coordinating anion; p+q is 2 or 3, matching the formal oxidation of said metal atom; L is a neutral Lewis donor molecule; b=0, 1, or 2; $R_1$-$R_5$, $R_7$-$R_9$ and $R_{12}$-$R_{14}$ are each, independently, hydrogen, optionally substituted hydrocarbyl, an inert functional group, or any two of $R_1$-$R_3$, $R_7$-$R_9$ and $R_{12}$-$R_{14}$ vicinal to one another taken together may form a ring; $R_6$ is hydrogen, optionally substituted hydrocarbyl, an inert functional group, or taken together with $R_7$ or $R_4$ to form a ring; $R_{10}$ is hydrogen, optionally substituted hydrocarbyl, an inert functional group, or taken together with $R_9$ or $R_4$ to form a ring; $R_{11}$ is hydrogen, optionally substituted hydrocarbyl, an inert functional group, or taken together with $R_5$ or $R_{12}$ to form a ring; and $R_{15}$ is hydrogen, optionally substituted hydrocarbyl, an inert functional group, or taken together with $R_5$ or $R_{14}$ to form a ring; and said process is carried out and at an ethylene pressure of less than 2.5 MPa.

In one embodiment, of the present invention the metal catalyst system used employs one or more bis-aryliminepyridine $MX_a$ complexes and a second compound which is capable of transferring an optionally substituted hydrocarbyl or hydride group to a metal atom M selected from Fe or Co, and which is also capable of abstracting an $X^-$ group from said metal atom.

In another embodiment, of the present invention the metal catalyst system used employs one or more bis-aryliminepyridine $MX_a$ complexes, a second compound which is capable of transferring an optionally substituted hydrocarbyl or hydride group to a metal atom M selected from Fe or Co, and a third compound which is capable of abstracting an $X^-$ group from said metal atom.

In the present invention certain terms are used as follows:

By "higher" in higher linear alpha olefins and higher alkyl-branched alpha olefins is meant molecules containing from 4 to 30 carbon atoms.

Examples of optionally substituted aromatic hydrocarbon rings and optionally substituted polyaromatic hydrocarbon moieties include phenyl, naphthyl, anthracenyl, phenanthracenyl, and the like and substituted derivatives thereof.

The term "optionally substituted aromatic hydrocarbon ring in combination with a metal, said optionally substituted aromatic hydrocarbon ring being π-co-ordinated to the metal" includes metallocene moieties and sandwich and metal-arene complexes. Thus, it will be appreciated by the person skilled in the art that, optionally, the metal may be additionally π-co-ordinated to a further optionally substituted aromatic hydrocarbon ring, which may be different to the optionally substituted aromatic hydrocarbon ring in Z which is directly bonded to the imine nitrogen atom and/or co-ordinated to other ligands commonly known in the art. It will be further appreciated that the optionally substituted aromatic hydrocarbon ring in Z which is directly bonded to the imine nitrogen atom and which is also π-co-ordinated to the metal, may comprise one or more heteroatoms in the ring, i.e., such that said optionally substituted aromatic hydrocarbon ring is an optionally substituted aromatic heterocyclic group. Similarly, the further optionally substituted aryl group that the metal may additionally be π-co-ordinated to, may comprise one or more heteroatoms in the ring. Said metal atom may conveniently be iron, cobalt, nickel, chromium, titanium and vanadium. Examples of such moieties include the radical derived from ferrocene, cobaltocene, nickelocene, chromocene, titanocene, vanadocene, bis-π-arene vanadium complex, mono-π-arene chromium tricarbonyl complex and similar heteroarene metal complexes, i.e. bis- or mono-π-thiene or pyrrole iron or chromium complexes.

The term "heterohydrocarbyl" refers to a hydrocarbyl group, additionally containing one or more heteroatoms. Said heteroatoms are preferably bonded to at least two carbons in the heterohydrocarbyl group. Preferred heteroatoms are nitrogen, oxygen and sulphur.

Said heterohydrocarbyl group may be an optionally substituted aromatic heterocyclic moiety; an optionally substituted polyaromatic heterocyclic moiety; an optionally substituted aliphatic heterocyclic moiety; or an optionally substituted aliphatic heterohydrocarbyl moiety.

Examples of heterohydrocarbyl groups include 1-pyrrolyl, 2-pyrrolyl, 3-pyrrolyl, furyl, thienyl, indenyl, imidazolyl, triazolyl, oxazolyl, isoxazolyl, carbazolyl, thiazolyl, benzothiazolyl, thiadiazolyl, pyrimidinyl, pyridyl, pyridazinyl, and the like and substituted derivatives thereof.

Hydrocarbyl group: a group containing only carbon and hydrogen. Unless otherwise stated, the number of carbon atoms is preferably between 1 and 30.

In the present invention, the phrase "optionally substituted hydrocarbyl" is used to describe hydrocarbyl groups optionally containing one or more "inert" heteroatom-containing functional groups. By "inert" is meant that the functional groups do not interfere to any substantial degree with the co-oligomerisation process. Non-limiting examples of such inert groups are fluoride, chloride, silanes, stannanes, ethers and amines with adequate steric shielding, all well-known to those skilled in the art. Said optionally substituted hydrocarbyl may include primary, secondary and tertiary carbon atom groups of the nature described below.

Inert functional group: a group other than optionally substituted hydrocarbyl which is inert under the process conditions. By "inert" is meant that the functional group does not interfere to any substantial degree with the co-oligomerisation process. Examples of inert functional groups include halide, ethers, and amines, in particular tertiary amines.

Primary carbon atom group: a —$CH_2$—R group wherein R may be hydrogen, a optionally substituted hydrocarbyl, inert functional group. Examples of primary carbon atom groups include —$CH_3$, —$C_2H_5$, —$CH_2Cl$, —$CH_2OCH_3$, —$CH_2N(C_2H_5)_2$, —$CH_2Ph$.

Secondary carbon atom group: a —CH—$R_2$ group wherein R may be optionally substituted hydrocarbyl, inert functional group. Examples of secondary carbon atom groups include —$CH(CH_3)_2$, —$CHCl_2$, —$CHPh_2$, —CH=$CH_2$, cyclohexyl.

Tertiary carbon atom group: a —C—R₃ group wherein R may be optionally substituted hydrocarbyl, inert functional group. Examples of tertiary carbon atom groups include —C(CH₃)₃, —CCl₃, —C═CPh, 1-Adamantyl, —C (CH₃)₂(OCH₃).

By a "ligand which may insert an olefin" is meant a ligand which is coordinated to a metal ion into which bond an ethylene molecule or an alpha-olefin may be inserted to initiate or propagate a co-oligomerisation reaction. In [bis-aryliminepyridine $MY_p.L_b^+$][$NC^-$]$_q$ complexes according to the present invention, Y may be hydride, alkyl or any other anionic ligand which may insert an olefin.

By "non-coordinating anion" is meant an anion which does not substantially coordinate to the metal atom M. Non-coordinating anions ($NC^-$) that may be suitably employed include bulky anions such as tetrakis [3,5-bis (trifluoromethyl)phenyl]borate ($BAF^-$), $(C_6F_5)_4B^-$, and anions of alkylaluminium compounds including $R_3AlX^-$, $R_2AlClX^-$, $RAlCl_2X^-$, and "$RAlOX^-$", wherein R is hydrogen, optionally substituted hydrocarbyl or an inert functional group, and X is halide, alkoxide or oxygen.

It will be appreciated by those skilled in the art that within the boundary conditions hereinbefore described, substituents $R_1$-$R_{15}$ may be readily selected to optimise the performance of the catalyst system and its economical application.

Substituents $R_1$-$R_5$, $R_7$-$R_9$, $R_{12}$-$R_{14}$ may independently be linked together and form cyclic structures.

In one embodiment of the present invention, $R_1$-$R_5$, $R_7$-$R_9$ and $R_{12}$-$R_{14}$ are each, independently, hydrogen, optionally substituted hydrocarbyl, an inert functional group, or any two of $R_1$-$R_3$, $R_7$-$R_9$ and $R_{12}$-$R_{14}$ vicinal to one another taken together may form a ring; $R_6$ is a primary carbon group, a secondary carbon group or a tertiary carbon group; and provided that:

when $R_6$ is a primary carbon group none, one or two of $R_{10}$, $R_{11}$ and $R_{15}$ are primary carbon groups, and the remainder of $R_{10}$, $R_{11}$ and $R_{15}$ are hydrogen;

when $R_6$ is a secondary carbon group none or one of $R_{10}$, $R_{11}$ and $R_{15}$ is a primary carbon group or a secondary carbon group and the remainder of $R_{10}$, $R_{11}$ and $R_{15}$ are hydrogen;

when $R_6$ is a tertiary carbon group all of $R_{10}$, $R_{11}$ and $R_{15}$ are hydrogen; and any two of $R_6$, $R_7$, $R_8$, $R_9$, $R_{10}$, $R_{11}$, $R_{12}$, $R_{13}$, $R_{14}$ and $R_{15}$ vicinal to one another, taken together may form a ring.

In another embodiment of the present invention, $R_1$-$R_5$, $R_7$-$R_9$ and $R_{12}$-$R_{14}$ are each, independently, hydrogen, optionally substituted hydrocarbyl, an inert functional group, or any two of $R_1$-$R_3$, $R_7$-$R_9$ and $R_{12}$-$R_{14}$ vicinal to one another taken together may form a ring; $R_6$ is hydrogen, optionally substituted hydrocarbyl, an inert functional group, or taken together with $R_7$ or $R_4$ to form a ring; $R_{10}$ is hydrogen, optionally substituted hydrocarbyl, an inert functional group, or taken together with $R_9$ or $R_4$ to form a ring; $R_{11}$ and $R_{15}$ are, independently, hydrogen or an inert functional group.

In a further embodiment of the present invention, $R_1$-$R_5$, $R_7$-$R_9$ and $R_{12}$-$R_{14}$ are each, independently, hydrogen, optionally substituted hydrocarbyl, an inert functional group, or any two of $R_1$-$R_3$, $R_7$-$R_9$ and $R_{12}$-$R_{14}$ vicinal to one another taken together may form a ring; $R_6$, $R_{10}$, $R_{11}$ and $R_{15}$ are identical and are each selected from fluorine or chlorine.

In another embodiment of the process of the present invention, the bis-arylimine pyridine complexes employed therein comprise a ligand of formula (IV),

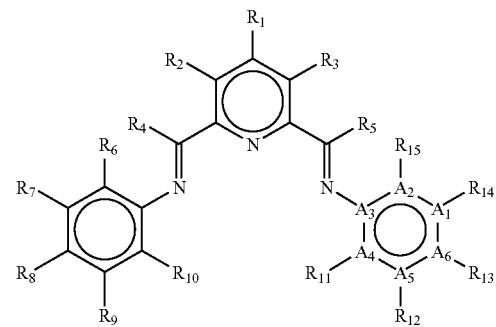

wherein $A_1$-$A_6$ are each, independently, carbon, nitrogen, oxygen, or sulphur; the atom group

may be optionally absent such that $A_1$ is directly bonded to $A_5$; and $R_1$-$R_{12}$, $R_{14}$-$R_{15}$ and, if present, $R_{13}$, are each, independently, hydrogen, optionally substituted hydrocarbyl, an inert functional group, or any two of $R_1$-$R_{15}$ vicinal to one another taken together may form a ring; with the proviso that when $A_1$-$A_5$, and $A_6$ if present, are all carbon, said atoms constitute the cyclopentadienyl or aryl part of a π-co-ordinated metal.

In a preferred embodiment of the present invention, in formula (IV), $R_1$-$R_3$, $R_7$-$R_9$, $R_{12}$, $R_{14}$ and, if present, $R_{13}$, are each, independently, hydrogen, optionally substituted hydrocarbyl, an inert functional group, or any two of $R_1$-$R_3$, $R_7$-$R_9$, $R_{12}$-$R_{14}$ vicinal to one another taken together may form a ring; and a) $R_6$ is an inert functional group or an optionally substituted hydrocarbyl, and $R_{10}$, $R_{11}$, and $R_{15}$ are, independently, hydrogen or halide; or b) $R_{11}$ is an inert functional group or an optionally substituted hydrocarbyl, and $R_6$, $R_{10}$, and $R_{15}$ are, independently, hydrogen or halide; or c) $R_6$ and $R_{10}$ are each, independently, inert functional group or a primary or secondary carbon atom group, provided that $R_6$ and $R_{10}$ are not both a secondary carbon atom group and $R_{11}$ and $R_{15}$ are, independently, hydrogen or halide; or d) $R_{11}$ and $R_{15}$ are each, independently, inert functional group or a primary or secondary carbon atom group, provided that $R_{11}$ and $R_{15}$ are not both a secondary carbon atom group and $R_6$ and $R_{10}$ are, independently, hydrogen or halide; or e) $R_6$ is taken together with $R_7$ to form a ring, $R_{10}$ is a primary carbon atom group, an inert functional group, or hydrogen and $R_{11}$ and $R_{15}$ are, independently, hydrogen or halide; or f) $R_{11}$ is taken together with $R_{12}$ to form a ring, $R_{15}$ is a primary carbon atom group, an inert functional group, or hydrogen and $R_6$ and $R_{10}$ are, independently, hydrogen or halide; or g) $R_6$ and $R_{10}$ are taken together with $R_7$ and $R_9$, respectively, to form rings and $R_{11}$ and $R_{15}$ are, independently, hydrogen or halide; or h) $R_{11}$ and $R_{15}$ are taken together with $R_{12}$ and $R_{14}$, respectively, to form rings and $R_6$ and $R_{10}$ are, independently, hydrogen or halide.

In formula (IV), substituents $R_{1-15}$, if present, may independently be linked together and form cyclic structures. Examples of such structures include the linking of, for example, $R_6$ with $R_7$, to form the basic naphthyl skeleton or a tetrahydronaphthyl unit.

Furthermore, it will be readily appreciated by any person who has mastered the basic principles of homogeneous catalysis, that in all of the above-mentioned ligands for use in the bis-arylimine pyridine complexes employed in the process of the present invention, substituent variations of $R_{1-5}$, $R_{7-9}$, and $R_{12-14}$, if present, may be selected so as to enhance other desirable properties of catalyst precursors and catalyst systems such as solubility in non-polar solvents or extending the range of suitable starting materials in their syntheses.

Preferred embodiments of the present invention employ ligands according to formula (I) and derivatives thereof, in which the following R groups appear:

$R_1$-$R_3$ are hydrogen; and/or $R_4$ and $R_5$ are methyl, hydrogen, benzyl or phenyl, preferably methyl, phenyl or hydrogen.

Preferred embodiments of the present invention employ ligands according to formulae (I), (II), (III) and (IV), and derivatives thereof, in which the following R groups appear:

$R_1$-$R_3$ are hydrogen; and/or $R_4$ and $R_5$ are methyl, hydrogen, benzyl or phenyl, preferably methyl, phenyl or hydrogen.

Preferred embodiments are ligands according to (IV) and derivatives thereof, in which the following R groups appear:

$R_1$-$R_3$ are hydrogen; and/or $R_4$ and $R_5$ are methyl, hydrogen or phenyl, preferably methyl; and/or

is absent and $A_1$-$A_5$ are carbon atoms, thereby constituting the cyclopentadienylide part of a ferrocenyl moiety; or $A_3$ is a nitrogen atom,

is absent and $A_1$, $A_2$, $A_4$, $A_5$ are carbon atoms, thereby constituting a 1-pyrrolyl ring; and/or Combinations of ortho-substituents in which $R_6$ is methyl, ethyl, iso-propyl, phenyl, tertiary-butyl, or linked to $R_7$ to form a naphthyl skeleton; $R_{10}$ is hydrogen, fluoride, or chloride; $R_{11}$ and $R_{15}$ are independently, hydrogen, fluoride or chloride and/or Combinations of ortho-substituents in which $R_6$ and $R_{10}$ are, independently, methyl, ethyl, or linked to $R_7$ and $R_9$, respectively, to form an anthracene skeleton, preferably methyl; $R_{11}$ and $R_{15}$ are, independently, hydrogen, fluoride or chloride.

It is particularly preferred that in formula (IV) $R_{11}$ and $R_{15}$ are, independently, hydrogen or fluoride.

Preferred ligands include:

a ligand of formula (II), wherein $R_1$-$R_3$ are hydrogen; $R_4$ and $R_5$ are methyl; $R_6$, $R_8$, $R_{10}$ are methyl; $R_7$, $R_9$ are hydrogen and Z is 1-pyrrolyl;

a ligand of formula (II), wherein $R_1$-$R_3$ are hydrogen; $R_4$ and $R_5$ are methyl; $R_6$, $R_8$, $R_{10}$ are methyl; $R_7$ and $R_9$ are hydrogen and Z is ferrocenyl;

a ligand of formula (III), wherein $R_1$-$R_3$ are hydrogen; $R_4$ and $R_5$ are methyl; $R_6$, $R_8$, and $R_{10}$ are methyl; $R_7$ and $R_9$ are hydrogen; $R_{11}$ and $R_{15}$ are hydrogen; $R_{12}$ and $R_{14}$ are hydrogen; and $R_{13}$ is tert-butyl;

a ligand of formula (III), wherein $R_1$-$R_3$ are hydrogen; $R_4$ and $R_5$ are methyl; $R_6$ and $R_7$ are taken together to form a six-membered aromatic ring; $R_8$ and $R_{10}$ are hydrogen; $R_9$ is hydrogen; $R_{11}$ and $R_{15}$ are hydrogen; $R_{12}$ and $R_{14}$ are hydrogen; and $R_{13}$ is tert-butyl;

a ligand of formula (III), wherein $R_1$-$R_3$ are hydrogen; $R_4$ and $R_5$ are methyl; $R_6$ is tert-butyl; $R_7$-$R_{10}$ are hydrogen; $R_{11}$ and $R_{15}$ are hydrogen; $R_{12}$ and $R_{14}$ are hydrogen; and $R_{13}$ is tert-butyl;

a ligand of formula (III), wherein $R_1$-$R_3$ are hydrogen; $R_4$ and $R_5$ are methyl; $R_6$, $R_8$ and $R_{10}$ are methyl; $R_7$ and $R_9$ are hydrogen; $R_{11}$ is fluorine; and $R_{12}$-$R_{15}$ are hydrogen;

a ligand of formula (III), wherein $R_1$-$R_3$ are hydrogen; $R_4$ and $R_5$ are methyl; $R_6$ is tert-butyl; $R_7$-$R_{10}$ are hydrogen; $R_{11}$, $R_{13}$ and $R_{15}$ are hydrogen; and $R_{12}$ and $R_{14}$ are methyl;

a ligand of formula (III), wherein $R_1$-$R_3$ are hydrogen; $R_4$ and $R_5$ are methyl; $R_6$ and $R_{10}$ are fluorine; $R_7$-$R_9$ are hydrogen; $R_{12}$ and $R_{15}$ are methyl; and $R_{11}$, $R_{13}$ and $R_{14}$ are hydrogen; and a ligand of formula (III), wherein $R_1$-$R_3$ are hydrogen; $R_4$ and $R_5$ are methyl; $R_7$-$R_9$ and $R_{12}$-$R_{14}$ are hydrogen; and $R_6$, $R_{10}$, $R_{11}$ and $R_{15}$ are fluorine.

a ligand of formula (III), wherein $R_1$-$R_3$ are hydrogen; $R_4$ and $R_5$ are methyl; $R_7$-$R_{10}$ are hydrogen; $R_6$ is methyl; $R_{11}$-$R_{14}$ are hydrogen; and $R_{15}$ is methyl.

In the bis-aryliminepyridine $MX_a$ complex, X may conveniently be halide, preferably chloride.

In a preferred embodiment of the bis-aryliminepyridine $MX_a$ complex, metal atom M is Fe and a is 2. In another preferred embodiment, metal atom M is Fe and a is 3.

Compounds which are capable of transferring an optionally substituted hydrocarbyl or hydride group to metal atom M, and which are also capable of abstracting an $X^-$ group from metal atom M include alkylaluminium compounds such as alkylaluminoxane and alkylaluminium halides. A preferred compound is methylaluminoxane.

Compounds which are capable of transferring an optionally substituted hydrocarbyl or hydride group to metal atom M include alkylaluminium compounds including alkyl aluminoxanes, alkyl lithium compounds, Grignards, alkyl tin and alkyl zinc compounds.

Compounds which are capable of abstracting an $X^-$ group from metal atom M include strong neutral Lewis acids such as $SbF_5$, $BF_3$ and $Ar_3B$, wherein Ar is a strong electron-withdrawing aryl group such as $C_6F_5$ or $3,5\text{-}(CF_3)_2C_6H_3$.

A neutral Lewis donor molecule is a compound which may suitably act as a Lewis base, such as ethers, amines, sulphides and organic nitriles.

The use of donor molecules (Lewis Bases) such as triethylamine or 2,6-di-tert-butylpyridine, and/or acceptor molecules (Lewis Acids) such as diethylzinc, may have a positive influence on the selectivity of the ethylene co-oligomerisation process.

Furthermore, Lewis acids such as tri-iso-butylaluminium (TIBA) may enhance the continuous operation of the Fe- or Co- catalysed ethylene co-oligomerisation by enabling the preparation of stable and clear catalyst precursor solutions, in contrast to MAO activated and solubilised catalyst precursor solutions, which may become turbid upon standing.

In the [bis-aryliminepyridine $MY_p.L_n^+][NC^-]_q$ complex according to the present invention, L may be a neutral Lewis donor molecule capable of being displaced by ethylene, or a vacant coordination site.

In the [bis-aryliminepyridine $MY_p.L_n^+][NC^-]_q$ complex according to the present invention, metal atom M is preferably Fe and the formal oxidation state of said metal atom may be 2 or 3.

The catalyst system may be formed by mixing together the complex and optional additional compounds, preferably in a solvent such as toluene or isooctane.

The mole ratio of $MX_n$ complex, second compound, and optionally third compound is not limited in the present invention.

It is possible to enhance the flexibility of an co-oligomerisation reaction by employing a mixture of one or more catalyst systems according to the present invention.

Such a quantity of the catalyst system is usually employed in the co-oligomerisation reaction mixture so as to contain from $10^{-4}$ to $10^{-9}$ gram atom, of metal atom M, in particular of Fe [II] or [III] metal, per mole of ethylene and/or alpha olefin to be reacted.

The co-oligomerisation reaction may be conveniently conducted over a range of temperatures from $-100°$ C. to $300°$ C., preferably in the range of from $0°$ C. to $200°$ C., and more preferably in the range of from $50°$ C. to $150°$ C.

The co-oligomerisation reaction is preferably carried out at an ethylene pressure of less than 2.0 MPa (20 bar(a)), and more preferably at an ethylene pressure between 0.1 MPa (1 bar(a)) and 1.6 MPa (16 bar(a)).

Alpha olefin co-monomer is generally present in a concentration of greater than 1 mol.l$^{-1}$, preferably in a concentration of greater than 2.5 mol.l$^{-1}$, and more preferably in a concentration of greater than 5 mol.l$^{-1}$ The conditions of temperature and pressure are preferably selected to yield a product slate with a K-factor within the range of from 0.40 to 0.90, preferably in the range of from 0.45 to 0.90. In the present invention, polymerisation is deemed to have occurred when a product slate has a K-factor greater than 0.9.

The co-oligomerisation reaction can be carried out in the gas phase or liquid phase, or mixed gas-liquid phase, depending upon the volatility of the feed and product olefins.

The co-oligomerisation reaction may be carried out in the presence of an inert solvent which may also be the carrier for the catalyst and/or feed olefins. Suitable solvents include alkanes, alkenes, cycloalkanes, and aromatic hydrocarbons.

For example, solvents that may be suitably used include hexane, isooctane, benzene, toluene, and xylene.

Reaction times of from 0.1 to 10 hours have been found to be suitable, dependent on the activity of the catalyst. The reaction is preferably carried out in the absence of air or moisture.

The co-oligomerisation reaction may be carried out in a conventional fashion. It may be carried out in a stirred tank reactor, wherein olefins and catalysts or catalyst precursors are added continuously to a stirred tank and reactants, products, catalysts, and unused reactants are removed from the stirred tank with the products separated and the catalysts and unused reactants recycled back to the stirred tank.

Alternatively, the reaction may be carried out in a batch reactor, wherein the catalyst precursors, and reactant olefins are charged to an autoclave, and after being reacted for an appropriate time, products are separated from the reaction mixture by conventional means, such as distillation.

After a suitable reaction time, the co-oligomerisation reaction can be terminated by rapid venting of the ethylene in order to deactivate the catalyst-system.

The resulting product composition may comprise linear alpha olefins and/or alkyl-branched alpha olefins.

In a preferred embodiment, the product composition may comprise linear alpha olefins and/or methyl-branched alpha olefins and/or ethyl-branched alpha olefins, that is to say wherein $R_{16}$ is methyl or ethyl.

The product composition of the present invention will generally comprise greater than 5% wt, preferably greater than 10% wt, more preferably greater than 15% wt, and most preferably greater than 25% wt alkyl-branched alpha olefins based on the total weight of linear alpha olefins and alkyl-branched alpha olefins in the product composition.

Said linear alpha olefins and/or alkyl-branched alpha olefins may have a chain length of from 4 to 100 carbon atoms, preferably 4 to 30 carbon atoms, and most preferably from 4 to 20 carbon atoms.

Product olefins can be recovered suitably by distillation and further separated as desired by distillation techniques dependent on the intended end use of the olefins.

The present invention will now be illustrated by the following Examples, which should not be regarded as limiting the scope of the present invention in any way.

General Procedures and Characterisation

All the operations with the catalyst systems were carried out under nitrogen atmosphere. All solvents used were dried using standard procedures.

Anhydrous toluene (99.8% purity) (ex. Aldrich) was dried over 4 Å molecular sieves (final water content of about 3 ppm).

Ethylene (99.5% purity) was purified over a column containing 4 Å molecular sieves and BTS catalyst (ex. BASF) in order to reduce water and oxygen content to <1 ppm.

1-Octene (99.8% 1-octene content; the remainder being 0.1% 1-hexene and 0.1% 1-decene) and 1-hexadecene (94.1% 1-hexadecene content; the remainder being 3.6% 1-tetradecene and 2.3% 1-octadecene) were SHOP alpha olefins obtained from Shell Chemicals and were purified by treatment with basic alumina and subsequent drying over 4 Å molecular sieves in a nitrogen atmosphere. 1-Heptene (99.3% 1-heptene content; the remainder being heptene isomers) was obtained from Aldrich and was used after drying over 4 Å molecular sieves in a nitrogen atmosphere.

1-Aminonaphthalene, 2,6-Diacetylpyridine, 3,5-dimethylaniline, 2,5-dimethylaniline, 2,4,6-trimethylaniline, 2-tert-butylaniline, 4-tert-butylaniline, 2,6-difluoroaniline, 2-fluoroaniline and anhydrous iron (II) chloride are available ex. Aldrich. 1-Aminopyrrole was purchased from TCI, Japan.

Ferrocenylamine was prepared according to the method outlined in the literature (D. van Leusen and B. Hessen, Organometallics, 2001, 20, 224-226).

The oligomers obtained were characterised by Gas Chromatography (GC), in order to evaluate oligomer distribution, using a HP 5890 series II apparatus and the following chromatographic conditions:

Column: HP-1 (cross-linked methyl siloxane), film thickness=0.25 µm, internal diameter=0.25 mm, length 60 m (by Hewlett Packard); injection temperature: $325°$ C.; detection temperature: $325°$ C.; initial temperature: $40°$ C. for 10 minutes; temperature programme rate: $10.0°$ C./minute; final temperature: $325°$ C. for 41.5 minutes; internal standard: n-hexylbenzene. Response factors for the even linear alpha olefins relative to n-hexylbenzene (internal standard) were determined using a standard calibration mixture. Response factors for the even-numbered branched alpha olefins, the odd-numbered linear and branched alpha olefins were assumed to be equal to the even linear alpha olefins of the same or similar carbon number. The yields of the $C_4$-$C_{30}$ olefins were obtained from the GC analysis, from which the K(linear)-factors were determined by regression analysis, generally using the $C_{10}$-$C_{28}$ data of the linear alpha olefins.

In the ethene/1-octene co-oligomerisation the 1-octene content was calculated from the regression analysis of the linear alpha olefins in the $C_{10}$-$C_{28}$ range. In the ethene/1-hexadecene co-oligomerisation the 1-hexadecene content was calculated from the regression analysis of the linear alpha olefins in the $C_{18}$-$C_{28}$ range.

The relative amounts of the linear (lin.) 1-hexene amongst all hexene isomers and the relative amount of linear (lin.) 1-dodecene amongst all dodecene isomers found from the GC analysis is used as a measure of the selectivity of the catalyst towards linear alpha-olefin formation.

The yields of the branched $C_{10}$-$C_{30}$ alpha olefins in case of ethene/1-octene co-oligomerisation, or the branched $C_{18}$-$C_{30}$ alpha olefins in case of ethene/1-hexadecene co-oligomerisation, were obtained from the GC analysis, from which the K(branched)-factors were determined by regression analysis. In the case of co-oligomerisation of ethene and 1-heptene the yields of the odd linear and branched $C_9$-$C_{29}$ alpha olefins were obtained from the GC analysis, from which their K(linear)-factor and their K(branched)-factor were determined by regression analysis.

The weight ratio of alkyl-branched 1-undecene(s) over alkyl-branched and linear 1-undecenes, the weight ratio of alkyl-branched 1-dodecene(s) over alkyl-branched and linear 1-dodecenes and the weight ratio of alkyl-branched 1-eicocene(s) over alkyl-branched and linear 1-eicocenes determined by GC analysis are used as a measure of the selectivity of the catalyst towards the formation of alkyl-branched alpha-olefins.

The NMR data were obtained at room temperature with a Varian 300 or 400 MHz apparatus. Structural assignments of linear alpha-olefins and by-products were made by comparison of $^1$H- and $^{13}$C-NMR spectra of reaction samples containing different amounts of various components. Characteristic resonances for olefinic and linear and branched aliphatic groups were taken from literature. Where deemed necessary, techniques allowing identification of carbon-carbon connectivities were applied to provide additional structural proof.

Catalyst Components

1. Preparation of 2,6-bis-[1-(2-methylphenylimino) ethyl]pyridine iron[II] chloride complex (X)

Complex X was prepared according to the method disclosed in WO-A-99/02472.

2. Preparation of 2-[1-(2,4,6-trimethylphenylimino) ethyl]-6-acetylpyridine (1)

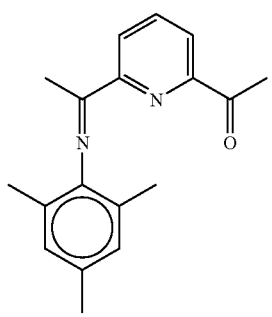

(1)

2,6-Diacetylpyridine (7.3 g, 44.8 mmol) and 2,4,6-trimethylaniline (5.74 g, 42.55 mmol) were dissolved in 450 ml of toluene. To this solution, 4 Å molecular sieves and a small amount of p-toluenesulphonic acid (0.22 mmol) were added. The mixture was refluxed for 16 hours. After filtration the solvent was removed in vacuo. Several crystallisations from ethanol yielded 3.42 g (28.7%) of monoimine (1). $^1$H-NMR (CDCl$_3$) δ 8.55 (d, 1H, Py-H$_m$), 8.11(d, 1H, Py-H$_m$), 7.92 (t, 1H, Py-H$_p$) 6.89 (s, 2H, ArH), 2.77(s, 3H, Me), 2.27 (s, 3H, Me), 2.22 (s, 3H, Me), 1.99 (s, 6H, Me).

3. Preparation of 2-[1-(2,4,6-trimethylphenylimino) ethyl]-6-[1-(4-tert-butylphenylimino)ethyl]pyridine (2)

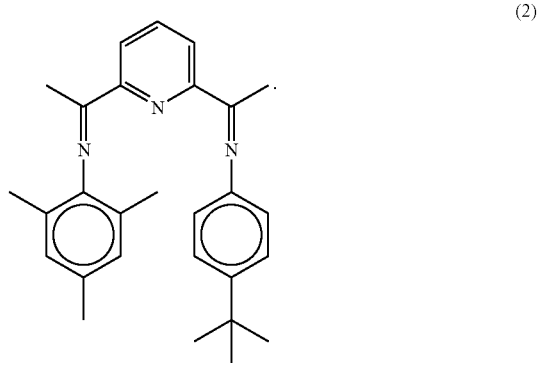

Monoimine (1, 2.8 g, 10 mmol) and 4-tert-butylaniline (1.49 g, 10 mmol) were dissolved in 100 ml of toluene. To this solution, 4 Å molecular sieves and a small amount of p-toluenesulphonic acid (0.1 mmol) were added. After standing for 5 days with addition of more 4 Å molecular sieves, the mixture was, refluxed for 2 hours. After filtration the solvent was removed in vacuo. The residue was washed with methanol and recrystallised from ethanol. Yield 2.4 g (.58%) of mixed diimine (2). $^1$H-NMR (CDCl$_3$) δ 8.42 (d, 1H, Py-H$_m$), 8.34 (d, 1H, Py-H$_m$), 7.86 (t, 1H, Py-H$_p$), 7.38 (d, 2H, ArH), 6.89 (s, 2H, ArH), 6.78 (d, 2H, ArH), 2.42 (s, 3H, Me), 2.29 (s, 3H, Me), 2.22 (s, 3H, Me), 2.00 (s, 6H, Me), 1.34 (s, 9H, Bu$^t$)

4. Preparation of 2-[1-(2,4,6-trimethylphenylimino) ethyl]-6-[1-(4-tert-butylphenylimino) ethyl] pyridine iron[II] chloride complex (3)

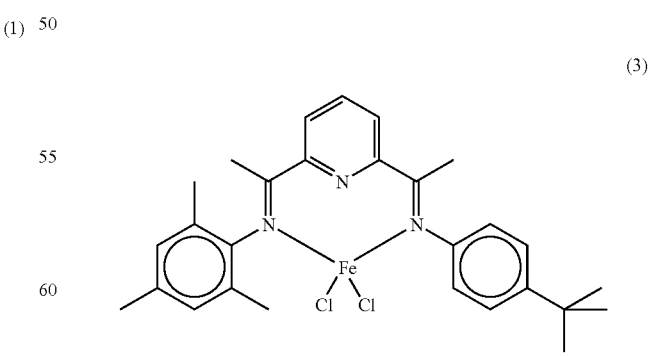

In an inert atmosphere a solution of 1.5 g diimine (2, 3.6 mmol) in 100 ml dichloromethane was added to 420 mg FeCl$_2$ (3.3 mmol) in 150 ml dichloromethane. The mixture was stirred for one week. The developed blue precipitate was isolated by filtration and dried in vacuo. Yield 1.5 g (84%) of iron complex (3). $^1$H-NMR (Cl2CDCDCl$_2$, broad signals) d 79.3 (1H, Py-H$_m$), 77.7 (1H, Py-H$_m$), 27.0 (1H, Py-H$_p$), 20.7 (3H, Me), 17.3 (6H, Me), 15.0 (2H, ArH), 14.3 (2H, ArH), 1.2 (9H, Bu$^t$), −2.6 (3H, MeC=N), −17.9 (2H, o-ArH), −32.1 (3H, MeC=N).

5. Preparation of 2,6-bis-[1-(2,6-difluorophenylimino) ethyl] pyridine (4)

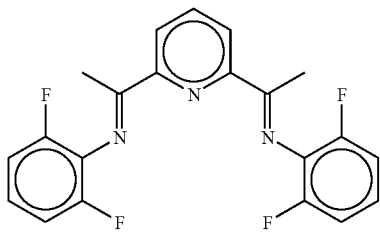

(4)

2,6-Diacetylpyridine (1.76 g, 10.8 mmol) and 2,6-difluoroaniline (2.94 g, 22.8 mmol) were dissolved in 50 ml of toluene. To this solution, 4 Å molecular sieves were added. After standing for 3 days, with addition of more 4 Å molecular sieves the mixture was filtered. The solvent was removed in vacuo. The residue was crystallised from ethanol. Yield of 4: 1 g (24%). $^1$H-NMR (CDCl$_3$) δ 8.44 (d, 2H, Py-H$_m$), 7.90 (t, 1H, Py-H$_p$), 7.05 (m, 2H, ArH) 6.96 (m, 4H, ArH), 2.44 (s, 6H, Me). $^{19}$F-NMR (CDCl$_3$) δ −123.6.

6. 2,6-bis-[1-(2,6-difluorophenylimino)ethyl] pyridine iron[II] chloride complex (5)

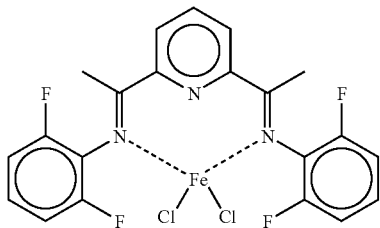

(5)

In an inert atmosphere 493 mg diimine (4, 1.27 mmol) was dissolved in 50 ml THF. FeCl$_2$ (162 mg , 1.28 mmol) in 10 ml THF was added. After stirring for 16 hours at room temperature, the solvent was removed in vacuo. Toluene (100 ml) was added. The blue precipitate was isolated by filtration, washed with pentane and dried in vacuo. Isolated 0.5 g (76%) of iron complex 5. $^1$H-NMR (Cl$_2$CDCDCl$_2$, broad signals) δ 75.5 (2H, Py-H$_m$), 39.6 (1H, Py-H$_p$), 15.7 (4H, ArH), −11.6 (2H, ArH), −22.4 (6H, MeC=N). $^{19}$F-NMR (Cl$_2$CDCDCl$_2$) δ −70.3.

7. Alternate preparation of 2,6-bis-[1-(2,6-difluorophenylimino)ethyl] pyridine iron[II] chloride complex (5')

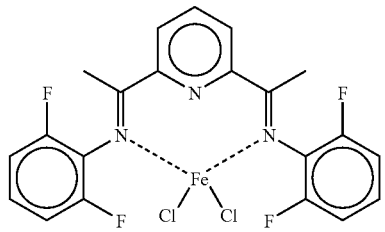

(5')

In an inert atmosphere a solution of 60 mg FeCl$_2$ (0.47 mmol) in 0.5 ml ethanol was slowly added to a solution of 260 mg diimine (4, 0.67 mmol) in a solvent mixture of 10 ml toluene and 6 ml pentane. The resulting blue precipitate was isolated by centrifugation, washed three times with toluene and dried in vacuo. Yield 210 mg (87%) of iron complex 5'. $^1$H-NMR (CD$_2$Cl$_2$, broad signals) δ 76.7 (2H, Py-H$_m$), 37.6 (1H, Py-H$_p$), 16.8 (4H, ArH), −10.2 (2H, ArH), −20.3 (6H, MeC=N). F-NMR (CD$_2$Cl$_2$) δ −75.

8. Preparation of 2-[1-(1-naphthylimino)ethyl]-6-acetylpyridine (6)

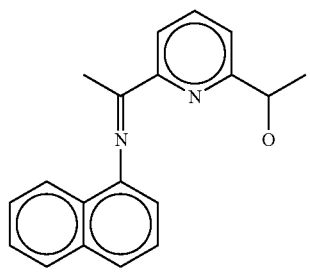

(6)

2,6-Diacetylpyridine (5.49 g, 33.6 mmol) and 1-aminonaphthalene (4.8 g, 33.5 mmol) were dissolved in 100 ml of toluene. To this solution molecular sieves (4 Å) were added. After standing for 20 hours at room temperature, the mixture was filtered. The solvent was removed in vacuo. The resulting mixture of 2,6-diacetylpyridine, 2,6-bis-[1-(1-naphthylimino)ethyl] pyridine and 2-[1-(1-naphthylimino)ethyl]-6-acetylpyridine was dissolved in 50 ml THF. The diiminepyridine by-product 2,6-bis-[1-(1-naphthylimino) ethyl]pyridine was removed by selective complexation to a metal halide. FeCl$_2$ (0.79 g , 6.23 mmol) was added in an inert atmosphere. After stirring for 16 hours at room temperature, the solvent was removed in vacuo. Toluene (100 ml) was added to the resulting mixture. The precipitated complex was filtered off over a small layer of silica, yielding a yellow solution. The solvent was removed vacuo. Crystallisation from ethanol yielded 3.25 g of 2-[1-(1-naphthylimino)ethyl]-6-acetylpyridine (6) (33.6%). $^1$H-NMR (CDCl$_3$) δ 8.65 (d, 1H, Py-H$_m$), 8.15 (d, 1H, Py-H$_m$), 7.95 (t, 1H, Py-H$_p$), 7.87 (d, 1H, ArH), 7.76 (d, 1H, ArH), 7.64 (d, 1H, ArH), 7.4-7.6 (m, 3H, ArH), 6.82 (d, 1H, ArH), 2.79 (s, 3H, Me), 2.38 (s, 3H, Me).

9. Preparation of 2-[1-(1-naphthylimino)ethyl]-6-[1-(4-tert-butylphenylimino)ethyl] pyridine (7)

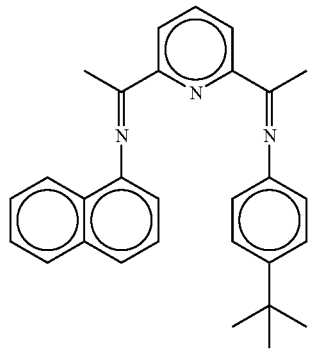
(7)

Monoimine (6, 1.25 g, 4.34 mmol) and 4-tert-butylaniline (0.65 g, 4.34 mmol) were dissolved in 50 ml of toluene. To this solution, molecular sieves (4 Å) were added. After standing for 16 hours the mixture was filtered. The solvent was removed in vacuo. The residue was recrystallised from ethanol. Yield 0.44 g (24%) of mixed diimine (7, 96% purity by NMR). H-NMR (CDCl$_3$) δ 8.51 (d, 1H, Py-H$_m$), 8.38 (d, 1H, Py-H$_m$), 7.91 (t, 1H, Py-H$_p$), 7.86 (d, 1H, ArH), 7.78 (d, 1H, ArH), 7.63 (d, 1H, ArH), 7.4-7.6 (m, 5H, ArH), 6.8-6.9 (m, 3H, ArH), 2.43 (s, 3H, Me), 2.37 (s, 3H, Me), 1.34 (s, 9H, Bu$^t$).

10. Preparation of 2-[1-(1-naphthylimino)ethyl]-6-[1-(4-tert-butylphenylimino)ethyl] pyridine iron[II] chloride complex (8)

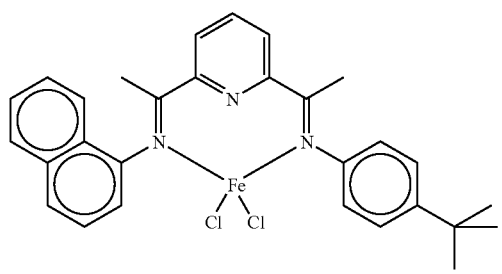

In an inert atmosphere, a solution of 440 mg diimine (7, 1.05 mmol) in 5 ml dichloromethane was added to 130 mg FeCl$_2$ (1.03 mmol) in 20 ml dichloromethane. The mixture was stirred for 9 days. Addition of 10 ml pentane yielded a blue precipitate, which was isolated by centrifugation and dried in vacuo. Yield 480 mg (85%) of iron complex (8) $^1$H-NMR (Cl$_2$CDCDCl$_2$), gave broad signals which were not further assigned.

11. Preparation of 2-[1-(2-tert-butylphenylimino)ethyl]-6-acetylpyridine (9)

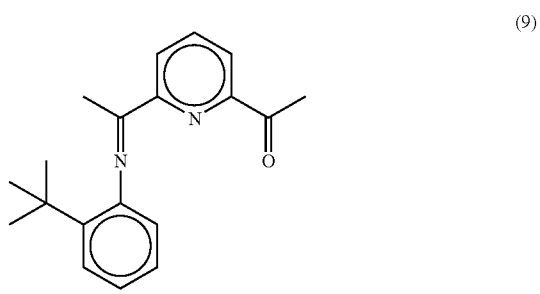
(9)

2,6-Diacetylpyridine (4.37 g, 26.78 mmol) and 2-tert-butylaniline (4.0 g, 26.8 mmol) were dissolved in 100 ml of toluene. To this solution, molecular sieves (4 Å) were added. After standing for 20 hours at room temperature, the mixture was filtered. The solvent was removed in vacuo.

The resulting mixture of 2,6-diacetylpyridine, 2,6-bis-[1-(2-tert-butylphenylimino)ethyl]pyridine and 2-[1-(2-tert-butylphenylimino)ethyl]-6-acetylpyridine was dissolved in 50 ml THF. The diiminepyridine by-product 2,6-bis-[1-(2-tert-butylphenylimino)ethyl]pyridine was removed by selective complexation to a metal halide.

FeCl$_2$ (0.79 g, 6.23 mmol) was added in an inert atmosphere. After stirring for 16 hours at room temperature, the solvent was removed in vacuo.

Toluene (100 ml) was added to the resulting mixture. The precipitated complex was filtered off over a small layer of silica, yielding a yellow solution. The solvent was removed in vacuo.

Crystallisation from ethanol yielded 2.8 g of 2-[1-(2-tert-butylphenylimino)ethyl]-6-acetylpyridine (9) (36%). $^1$H-NMR (CDCl$_3$) δ 8.48 (d, 1H, Py-H$_m$), 8.10 (d, 1H, Py-H$_m$), 7.93 (t, 1H, Py-H$_p$), 7.41 (d, 1H, ArH), 7.17 (t, 1H, ArH), 7.07 (t, 1H, ArH), 6.51 (d, 1H, ArH), 2.77 (s, 3H, Me), 2.38 (s, 3H, Me), 1.33 (s, 9H, Bu$^t$).

12. Preparation of 2-[1-(2-tert-butylphenylimino)ethyl]-6-[1-(4-tert-butylphenylimino)ethyl] pyridine (10)

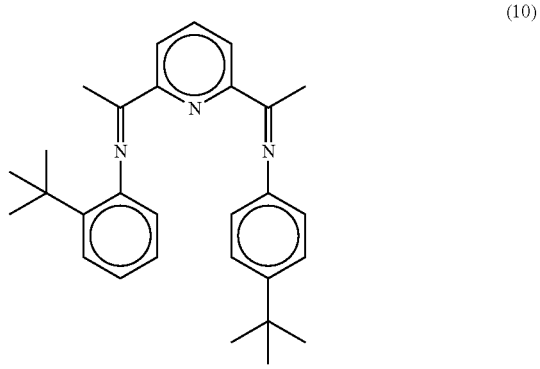
(10)

Monoimine (9, 1.06 g, 3.6 mmol) and 4-tert-butylaniline (0.56 g, 3.75 mmol) were dissolved in 25 ml of toluene. To this solution, molecular sieves (4 Å) were added. After standing for 60 hours the mixture was filtered. The solvent was removed in vacuo. The residue was recrystallised from ethanol. Yield 0.81 g (53%) of mixed diimine (10). $^{1}$H-NMR (CDCl$_3$) δ 8.36 (d, 1H, Py-H$_m$), 8.34 (d, 1H, Py-H$_m$), 7.88 (t, 1H, Py-H$_p$), 7.4 (m, 3H, ArH), 7.18 (t, 1H, ArH), 7.07 (t, 1H, ArH), 6.78 (d, 2H, ArH), 6.54 (d, 1H, ArH), 2.42 (s, 3H, Me), 2.38 (s, 3H, Me), 1.35 (s, 9H, Bu$^t$),1.34 (s, 9H, Bu$^t$).

13. Preparation of 2-[1-(2-tert-butylphenylimino) ethyl]-6-[1-(4-tert-butylphenylimino)ethyl] pyridine iron[II] chloride complex (11)

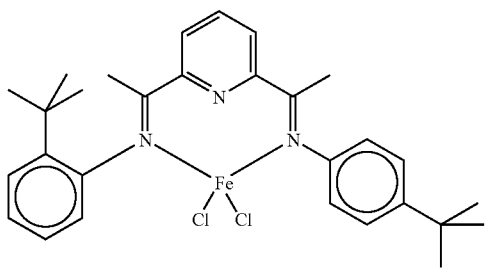

(11)

In an inert atmosphere, a solution of 640 mg diimine (10, 1.5 mmol) in 10 ml dichloromethane was added to 182 mg FeCl$_2$ (1.44 mmol) in 20 ml dichloromethane. The mixture was stirred for 16 hrs. Addition of 20 m] pentane yielded a blue precipitate. Isolation and drying in vacuo yielded 650 mg (82%) of iron complex (11). $^{1}$H-NMR (CD$_2$Cl$_2$, broad signals) δ 81.9 (1H, Py-H$_m$), 77.5 (1H, Py-H$_m$), 30.4 (1H, Py-H$_p$), 16.4 (1H, ArH), 13.8 (2H, ArH), 6.3 (1H, ArH), 1.5 (9H, Bu$^t$), 1.1 (9H, Bu$^t$), −1.0 (3H, MeC═N), −12.7 (1H, ArH), −21.3 (2H, o-ArH), −33.1 (3H, MeC═N), −33.7 (1H, o-ArH).

14. Preparation of 2-[1-(2-tert-butylphenylimino) ethyl]-6-[1-(3,5-dimethylphenylimino)ethyl] pyridine (12)

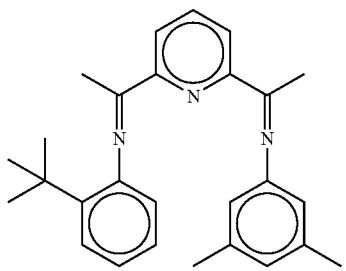

(12)

Monoimine (9,1.13 g, 3.87 mmol) and 3,5-dimethylaniline (0.5 g, 4.13 mmol) were dissolved in 25 ml of toluene. To this solution, molecular sieves (4 Å) were added. After standing for 60 hours the mixture was filtered. The solvent was removed in vacuo. The residue was recrystallised from ethanol. Yield 0.79 g (52%) of mixed diimine (12). $^{1}$H-NMR (CDCl$_3$) δ 8.37 (d, 1H, Py-H$_m$), 8.32 (d, 1H, Py-H$_m$), 7.87 (t, 1H, Py-H$_p$), 7.42 (d, 1H, ArH), 7.18 (t, 1H, ArH), 7.07 (t, 1H, ArH), 6.76 (s, 1H, ArH), 6.54 (d, 1H, ArH), 6.46 (s, 2H, ArH), 2.40 (s, 3H, Me), 2.39 (s, 3H, Me), 2.33 (s, 3H, Me), 1.36 (s, 9H, Bu$^t$).

15. Preparation of 2-[1-(2-tert-butylphenylimino) ethyl]-6-[1-(3,5-dimethylphenylimino)ethyl] pyridine iron[II] chloride complex (13)

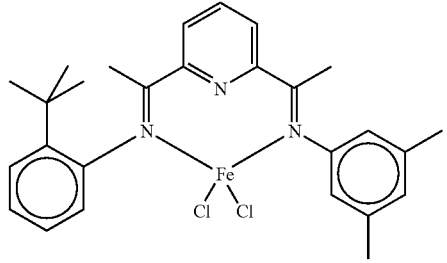

(13)

In an inert atmosphere, a solution of 617 mg diimine (12, 1.55 mmol) in 10 ml dichloromethane was added to 187 mg FeCl$_2$ (1.48 mmol) in 20 ml dichloromethane. The mixture was stirred for 16 hours. Addition of 20 ml pentane yielded a blue precipitate. Cooling to −30 °C. yielded a second amount of blue precipitate. Isolation and drying in vacuo yielded 660 mg (85%) of iron complex (13) $^{1}$H-NMR (CD$_2$Cl$_2$, broad signals) δ 81.5 (1H, Py-H$_m$), 76.9 (1H, Py-H$_m$), 37.6(1H, Py-H$_p$), 16.1 (1H, ArH), 1.2 (1H, ArH), 1.0 (9H, Bu$^t$), −2.7 (3H, MeC═N), −5.6 (6H, Me), −11.7 (1H, ArH), −13.5 (1H, ArH), −25.6 (2H, o-ArH), −35.7 (3H, MeC═N), −37.4 (1H, o-ArH).

16. Preparation of 2-[1-(2,4,6-trimethylphenylimino) ethyl]-6-[1-(2-fluorophenylimino)ethyl] pyridine (14)

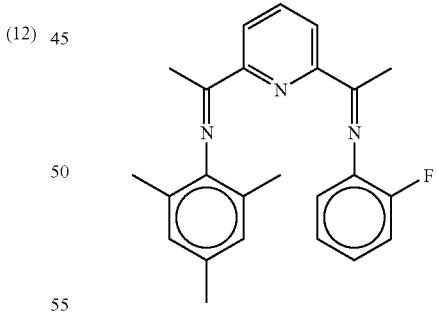

(14)

Monoimine (1, 1.0 g, 3.57 mmol) and 2-fluoroaniline (398 mg, 3.57 mmol) were dissolved in 50 ml of toluene. To this solution, 4 Å molecular sieves were added. After standing for 20 hours, with addition of more molecular sieves, the mixture was filtered. The solvent was removed in vacuum and the oily residue was warmed in ethanol (50° C.). The yellow solid, which precipitated after cooling at −20° C., was filtered off and dried in vacuo. Yield 300 mg (23%) of mixed diimine (14).

$^1$H-NMR (CDCl$_3$) δ 8.45 (d, 1H, Py-H$_m$), 8.38 (d, 1H, Py-H$_m$), 7.88 (t, 1H, Py-H$_p$), 7.1 (m, 4H, ArH), 6.93 (dd, 2H, ArH), 6.89 (s, 2H, ArH), 2.41 (s, 3H, Me), 2.29 (s, 3H, Me), 2.22 (s, 3H, Me), 2.00 (s, 6H, Me). $^{19}$F-NMR (CDCl$_3$) δ −126.8.

17. Preparation of 2-[1-(2,4,6-trimethylphenylimino) ethyl]-6-[1-(2-fluorophenylimino)ethyl] pyridine iron[II] chloride complex (15)

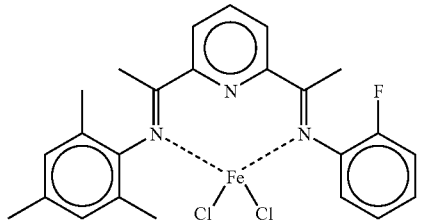

(15)

In an inert atmosphere, a solution of 270 mg diimine (14, 0.72 mmol) in 5 ml dichloromethane was added to 87 mg FeCl$_2$ (0.67 mmol) in 20 ml dichloromethane. The mixture was stirred for 20 hours. Addition of 10 ml pentane yielded a blue precipitate, which was isolated by centrifugation and dried in vacuo. Yield 175 mg (51%) of iron complex (15).

$^1$H-NMR (CD$_2$Cl$_2$, broad signals, selective data) δ 84.5 (1H, Py-H$_m$), 80.4 (1H, Py-H$_m$), 21.2 (1H, Py-H$_p$), 4.5 (3H, MeC=N), −24.5 (1H, o-ArH), −38.1 (3H, MeC=N). $^{19}$F-NMR (CD$_2$Cl$_2$) δ− 95.0.

18. Preparation of 2-[1-(2,4,6-trimethylphenylimino) ethyl]-6-[1-(1-pyrrolylimino)ethyl]pyridine (16)

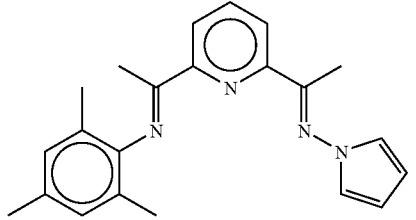

(16)

Monoimine ((1), 3.0 g, 10.7 mmol) and 1-aminopyrrole (1.0 g, 12.18 mmol) were dissolved in 50 ml of toluene. To this solution, molecular sieves (4 Å) were added. After standing for 40 hours the mixture was filtered. The solvent was removed in vacuo. The residue was recrystallised from ethanol. Yield 1.85 g (50%) of mixed diimine (16).

$^1$H-NMR (CDCl$_3$) δ 8.42 (d, 1H, Py-H$_m$), 8.29 (d, 1H, Py-H$_m$), 7.86 (t, 1H, Py-H$_p$), 6.93 (m, 2H, Pyrrole-H), 6.88 (s, 2H, ArH), 6.26 (m, 2H, Pyrrole-H), 2.67 (s, 3H, Me), 2.28 (s, 3H, Me), 2.20 (s, 3H, Me), 2.00 (s, 6H, Me).

19. Preparation of 2-[1-(2,4,6-trimethylphenylimino) ethyl]-6-[1-(1-pyrrolylimino)ethyl]pyridine iron[II] chloride complex (17)

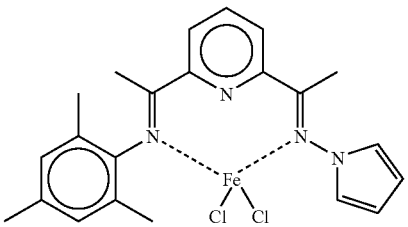

(17)

In an inert atmosphere, a solution of 103 mg FeCl$_2$ (0.81 mmol) in 0.7 ml ethanol was slowly added to a solution of 400 mg diimine ((16), 1.16 mmol) in a solvent mixture of 10 ml toluene and 6 ml pentane. The green-brown precipitate was isolated by centrifugation, washed three times with toluene and dried in vacuo. Yield 375 mg (98%) of iron complex (17).

$^1$H-NMR (CD$_2$Cl$_2$, broad signals, not assigned) δ 88.1 (1H), 72.4 (1H), 29.9 (3H), 19.5 (3H), 16.9 (6H), 13.5 (2H), 8.8 (2H), 5.8 (2H), 2.9 (1H), −45.1 (3H).

20. Preparation of 2-[1-(2,6-difluorophenylimino) ethyl]-6-acetylpyridine (18)

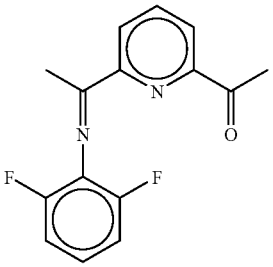

(18)

2,6-Diacetylpyridine (4.04 g, 24.7 mmol) and 2,6-difluoroaniline (3.2 g, 24.7 mmol) were dissolved in 50 ml of toluene. To this solution, molecular sieves (4 Å) were added. After standing for 5 days at room temperature, the mixture was filtered. The solvent was removed in vacuo. From the resulting mixture of 2,6-diacetylpyridine, monoimine, and diimine. Most of the 2,6-diacetylpyridine was removed by sublimation in vacuo at 80-90° C. The residue contained based on $^1$H-NMR data 0.35 mmol 2,6-diacetylpyridine, 1.28 mmol diimine and 5.46 mmol monoimine. This mixture was reacted with 162 mg (1.28 mmol) FeCl$_2$ in 10 ml THF to remove the diimine. After stirring for 16 h at room temperature, the solvent was removed in vacuo. Toluene (50 ml) was added to the resulting mixture. The precipitated complex was filtered off over a small layer of silica, yielding a yellow solution. The solvent was removed in vacuo. Crystallisation from ethanol yielded 1.35 g of 2-[1-(2,6-difluorophenylimino)ethyl]-6-acetylpyridine (18) (19.8%).

$^1$H-NMR (CDCl$_3$): δ 8.52 (d, 1H, Py-H$_m$), 8.12 (d, 1H, Py-H$_m$), 7.92 (t, 1H, Py-H$_p$), 7.03 (m,1H, ArH), 6.97 (m, 2H, ArH), 2.77 (s, 3H, Me), 2.43 (s, 3H, Me). $^{19}$F-NMR (CDCl$_3$): δ −123.6.

21. Preparation of 2-[1-(2,6-difluorophenylimino)ethyl]-6-[1-(2,5-dimethylphenylimino)ethyl]pyridine (19)

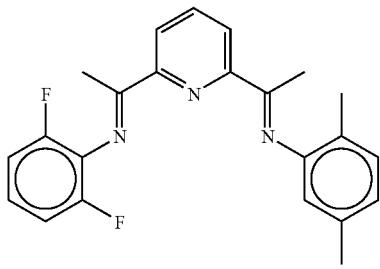

(19)

Monoimine (18, 0.86 g, 3.13 mmol) and 2,5-dimethylaniline (0.40 g, 3.3 mmol) were dissolved in 25 ml of toluene. To this solution, molecular sieves (4 Å) were added. After standing for 3 days the mixture was filtered. The solvent was removed in vacuo. The residue was crystallised from ethanol. A mixture of 2-[1-(2,6-difluorophenylimino)ethyl]-6-[1-(2,5-dimethylphenylimino)ethyl]pyridine and 2,6-bis{2-[1-(2,5-dimethylphenylimino)ethyl]}pyridine was isolated. In THF 2,6-bis{2-[1-(2,5-dimethylphenylimino)ethyl]}pyridine was co-ordinated to $FeCl_2$. The solvent was removed in vacuo. Toluene (10 ml) was added to the resulting mixture. The precipitated complex was filtered off over a small layer of silica, yielding a yellow solution. The solvent was removed in vacuo. Crystallisation from ethanol yielded 40 mg (3%) of 2-[1-(2,6-difluorophenylimino)ethyl]-6-[1-(2,5-dimethylphenylimino)ethyl]pyridine (19).

$^1$H-NMR (CDCl$_3$) δ 8.41 (d, 2H, Py-H$_m$), 7.89 (t, 1H, Py-H$_p$), 6.8-7.2 (m, 5H, ArH), 6.50 (s, 1H, ArH), 2.44 (s, 3H, Me), 2.32 (s, 6H, Me), 2.05 (s, 3H, Me). $^{19}$F-NMR (CDCl$_3$): δ −123.4

22. Preparation of 2-[1-(2,6-difluorophenylimino)ethyl]-6-[1-(2,5-dimethylphenylimino)ethyl]pyridine iron[II] chloride complex (20)

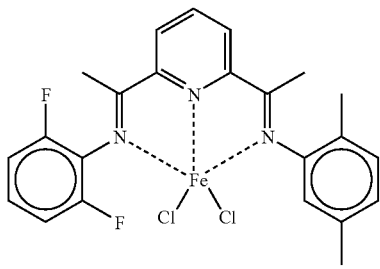

(20)

In an inert atmosphere a solution of 35 mg diimine (19, 0.093 mmol) in 5 ml dichloromethane was added to 11 mg FeCl$_2$ (0.086 mmol) in 10 ml dichloromethane. The mixture was stirred for 16 hours. After addition of 5 ml pentane the resulting blue precipitate was isolated by centrifugation, washed with pentane and dried in vacuo. Yield 40 mg (90%) of iron complex 20.

$^1$H-NMR (Cl$_2$CDCDCl$_2$, broad signals) δ 78.6 (1H, Py-H$_m$), 75.0 (1H, Py-H$_m$), 37.9 (1H, Py-H$_p$), 19.8 (1H, ArH), 16.6 (3H, Me) 15.8 (1H, ArH), 15.6 (1H, ArH), −8.2 (3H, Me) −9.7 (1H, ArH), −10.8 (3H, MeC=N), −15.7 (1H, ArH), −22.4 (1H, ArH), −29.8 (3H, MeC=N). $^{19}$F-NMR (Cl$_2$CDCDCl$_2$) δ −62.7 and −67.4.

23. Preparation of 2-[1-(2,4,6-trimethylphenylimino)ethyl]-6-[1-(ferrocenylimino)ethyl]pyridine (21)

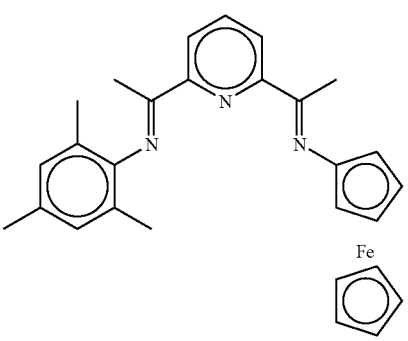

(21)

Monoimine 2-[1-(2,4,6-trimethylphenylimino)ethyl]-6-acetylpyridine (1, 263 mg, 0.94 mmol) and ferrocenylamine (280 mg, 1.03 mmol) were dissolved in 40 ml of toluene. To this solution, molecular sieves (4 Å) were added. After standing for 16 hours the mixture was filtered. The solvent was removed in vacuo. The residue was recrystallised from ethanol. Yield 180 mg (41%) of mixed diimine 21.

$^1$H-NMR (CD$_2$Cl$_2$) δ 8.36 (dd, 2H, Py-H$_m$), 7.85 (t, 1H, Py-H$_p$), 6.88 (s, 2H, ArH), 4.46 (t, 2H, CpH), 4.25 (t, 2H, CpH), 4.20 (s, 5H, CpH), 2.55 (s, 3H, Me), 2.27 (s, 3H, Me), 2.20 (s, 3H, Me), 1.98 (s, 6H, Me).

24. Preparation of 2-[1-(2,4,6-trimethylphenylimino)ethyl]-6-[1-(ferrocenylimino)ethyl]pyridine iron[II] chloride complex (22)

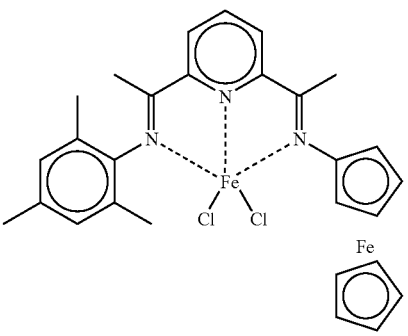

(22)

In an inert atmosphere a solution of 153 mg diimine (21, 0.33 mmol) in 5 ml dichloromethane was added to 41 mg FeCl$_2$ (0.32 mmol) in 5 ml dichloromethane. The mixture was stirred for 16 h. The blue-gray precipitate was isolated by centrifugation, washed with hexane and dried in vacuo. Yield 170 mg (89%) of iron complex 22.

$^1$H-NMR (CD$_2$Cl$_2$, broad signals, selected data) δ 88.6 (1H, Py-H$_m$), 76.7 (1H, Py-H$_m$), 21.3 (3H, Me), 16.3 (6H, Me), 2.8 (5H, CpH), −11.5 (3H, MeC=N).

25. Methylaluminoxane (MAO)

The MAO-solution in toluene (Eurecen AL 5100/10T, batch: B7683; [Al]=4.88% wt, TMA=35.7 wt % (calculated), Molecular mass=900 g/mol) used was ex. Witco GmbH, Bergkamen, Germany.

Catalyst System Preparation

Catalyst preparation was carried out under nitrogen in a Braun MB 200-G dry box.

The iron complex (typically about 10 mg) was placed in a glass bottle sealed by a septum; the MAO-solution (4.0 g), of the above mentioned grade, was added and stirred for 2 minutes. This yielded generally a dark-coloured solution, which sometimes contained some precipitate. Thereafter toluene (9.0 g) was added and the solution was stirred for another 10 min. Immediately hereafter, part of this solution was used in the oligomerisation reaction (see Table 1 for the amounts used).

Oligomerisation Experiments

Oligomerisation experiments were carried out in a 1-litre steel autoclave equipped with jacket cooling with a heating/cooling bath (ex. Julabo, model no. ATS-2) and a turbine/gas stirrer and baffles. In order to remove traces of water from the reactor, it was evacuated overnight at <10 Pa, at 70° C. The reactor was scavenged by introducing 250 ml toluene and MAO (0.3-1.2 g solution) and subsequent stirring at 70° C. under nitrogen pressure of 0.4-0.5 MPa for 30 min. The reactor contents were discharged via a tap in the base of the autoclave. The reactor was evacuated to 0.4 kPa and loaded with about 250 ml toluene, 1-heptene, 1-octene or 1-hexadecene (the precise amounts are mentioned in Table 1) and heated to 40° C. and pressurised with ethylene to the pressure indicated in Table 1 or in the description of the experiment. The MAO-solution (typically 0.5 g) was then added to the reactor with the aid of toluene (the total volume injected was 30 ml, using a procedure similar to the injection of the catalyst; see below) and the stirring at 800 rpm was continued for 30 minutes. The catalyst system prepared as described above and in an amount as described in Table 1, was introduced into the stirred reactor using an injection system with the aid of toluene (the total volume injected was 30 ml: the catalyst solution diluted with toluene to 10 ml was injected and the injector system was rinsed twice with 10 ml toluene). Addition of the catalyst solution resulted in an exotherm (generally 5-20° C.), which reached a maximum within 1 minute and was followed by rapid establishment of the temperature and pressure indicated in Table 1. Temperature and pressure were monitored throughout the reaction, as well as ethylene consumption, whilst maintaining a constant ethylene pressure. After consuming a certain volume ethylene, the oligomerisation. was stopped by rapid venting of the ethylene, decanting the product mixture into a collection bottle using a tap in the base of the autoclave. Exposure of the mixture to air resulted in rapid deactivation of the catalyst.

After addition of n-hexylbenzene (0.5-3.5 g) as internal standard to the crude product the amount of $C_4$-$C_{30}$ olefins was determined by gas chromatography, from which the (apparent) Schulz-Flory K(linear)-factor was determined by regression analysis, generally using the $C_{10}$-$C_{28}$ data of the linear alpha olefins. By "apparent" is meant in the case that there is a small deviation from a Schulz-Flory distribution. In the ethene/1-octene co-oligomerisation, the 1-octene content was calculated from the regression analysis of the linear alpha olefins in the $C_{10}$-$C_{28}$ range. In the ethene/1-hexadecene co-oligomerisation, the 1-hexadecene content was calculated from the regression analysis of the linear alpha olefins in the $C_{18}$-$C_{28}$ range. The data are reported in Table 1.

The amount of solids in the product was determined as follows. The crude reaction product was centrifuged at 4000 rpm for 30 min after which the clear upper layer was decanted. The lower layer consisting of solid olefins, toluene and a minor amount of liquid olefins was mixed with 500 ml acetone using a high-shear mixer (Ultra-Turrax, type TP 18-10). The mixture was centrifuged under the above-mentioned conditions. The lower layer was mixed with 200 ml acetone and filtered off over a glass filter (porosity P3). The solid product was dried for 24 hours at 70° C. at <1 kPa, weighed and its <$C_{32}$ contents determined by gas chromatography of a 1,2-dichlorobenzene or a 1,2,4-trichlorobenzene solution of the solids. The amounts of solids reported in Table 1 are the isolated solids having a carbon number >$C_{30}$.

The relative amounts of the linear (lin.) 1-hexene amongst all hexene isomers and the relative amount of the linear (lin.) 1-dodecene amongst all dodecene isomers were evaluated by GC analysis and are reported in Table 1.

The yields of the branched $C_{10}$-$C_{30}$ alpha olefins in case of ethene/1-octene co-oligomerisation, or the branched $C_{18}$-$C_{30}$ alpha olefins in case of ethene/1-hexadecene co-oligomerisation, and the yields of the odd linear and branched $C_9$-$C_{29}$ alpha olefins in the case of co-oligomerisation of ethene and 1-heptene were obtained by GC analysis. K(linear)-factors and/or K(branched)-factors were determined accordingly by regression analysis. These data are given in Table 1 and/or in the detailed description of the experiments.

The weight ratio of alkyl-branched 1-undecene(s) over alkyl-branched and linear 1-undecenes, the weight ratio of alkyl-branched 1-dodecene(s) over alkyl-branched and linear 1-dodecenes and the weight ratio of alkyl-branched 1-eicocene(s) over alkyl-branched and linear 1-eicocenes determined by GC analysis are reported in Table 1.

EXAMPLE 1

Iron complex 3, pre-activated in the manner described in the "Catalyst System Preparation", was employed in a 1-litre steel autoclave, loaded with 0.5 g MAO and toluene (total volume 310 ml), in an ethylene oligomerisation experiment at 1.6 MPa ethylene pressure. After an ethylene consumption of 118.2 g the reaction was stopped, giving rise to 110.6 g of linear $C_4$-$C_{30}$ alpha olefins and 2.5 g of solids >$C_{30}$. The total amount of ethylene oligomerisation product 113.1 g is slightly less than the ethylene uptake, which is attributed to loss of part of the volatile 1-butene and the formation small amounts of by-products.

The linear alpha olefins showed an almost perfect Schulz-Flory (S-F) distribution with K-factor of 0.72, as derived from regression analysis using the $C_{10}$-$C_{28}$ contents, determined by GC (Regression statistics: $R^2$=1.00; standard error=0.01 from 10 observations).

The Turn Over Frequency (T.O.F.) was 4.65E+07 mol ethylene/mol Fe*h.

The (linear) 1-hexene and 1-dodecene purity were 99.5 and 97.7% wt, respectively. The amounts of branched $C_{12}$ alpha olefin and branched $C_{20}$ alpha olefin were <2 and <3% wt, respectively.

The details of Example 1 are given in Table 1.

EXAMPLE 2

Example 2 is a repeat of Example 1 apart from the fact that part of the toluene has been replaced by 1-heptene. The ethylene uptake of 118.3 g resulted in 110.3 g even-numbered linear $C_4$-$C_{30}$ alpha olefins, whilst 2.0 g solids >$C_{30}$ were isolated. Besides these products GC analyses showed formation distributions of odd-numbered linear and branched alpha olefins. The odd ($C_9$-$C_{29}$) linear alpha olefins amounted to 1.7 g, whilst the odd branched alpha olefins amounted to 1.1 g.

The linear $C_{10}$-$C_{28}$ alpha olefins showed a Schulz-Flory distribution, as derived from regression analysis, with a K(even-linear)-factor of 0.69 ($R^2$=1.00; standard error <0.01 for 10 observations). Regression analysis of the odd-numbered linear $C_9$-$C_{21}$ alpha olefins and the odd-numbered branched $C_9$-$C_{21}$ alpha olefins gave Schulz-Flory distributions, having a K(odd-linear) of 0.70 ($R^2$=1.00; standard error=0.02 for 7 observations) and a K(odd-branched) of 0.68 ($R^2$=1.00; standard error=0.02 for 7 observations), respectively.

The T.O.F. was 2.13E+07 mol ethylene/mol Fe*h.

The linear (lin.) 1-hexene and 1-dodecene purity were 99.0 and 96.1% wt, respectively.

The details of Example 2 are given in Table 1.

EXAMPLE 3

Example 3 was a repeat of Example 2, but with the 1-heptene replaced by a 1-octene. After an ethylene consumption of 118.0 g the reaction was stopped, giving rise to 125.4 g of linear $C_4$-$C_{30}$ alpha olefins and 9.7 g of solids >$C_{30}$. The excess of linear alpha olefin production is attributed to incorporation of starting 1-octene in the final products as shown in Example 2.

The linear alpha olefins had a Schulz-Flory distribution with K-factor of 0.73, as derived from regression analysis using the $C_{10}$-$C_{28}$ contents, determined by GC (Regression statistics: $R^2$=1.00; standard error=0.02 from 10 observations).

The T.O.F. was 3.43E+07 mol ethylene/mol Fe*h.

The linear 1-hexene and linear 1-dodecene purity were 99.5 and 91.9% wt, respectively.

GC and NMR data showed the by-products to be mainly methyl-branched (Me-branched) alpha olefins having a K-factor of 0.71 ($R^2$=0.98; standard error=0.06 from 10 observations).

Details of the reaction are provided in Table 1.

EXAMPLE 4

Example 4 is a repeat of Example 3, but now using 1-hexadecene instead of 1-octene. The amount of linear alpha-olefins was in excess of the amount of ethylene consumed: 116.3 vs. 111.5 g, respectively. The linear alpha olefins had a Schulz-Flory distribution with K-factor of 0.72, as derived from regression analysis using the $C_{18}$-$C_{28}$ contents, determined by GC (Regression statistics: $R^2$=1.00; standard error=0.01 from 6 observations), as shown in FIG. 1. It is clear from this Figure that 1,2-insertion of 1-hexadecene occurs, as confirmed by Example 2.

The T.O.F. was 1.42E+06 mol ethylene/mol Fe*h.

The linear 1-hexene and 1-dodecene purity were 99.6 and 97.9% wt. The amount of alkyl-branched $C_{20}$ alpha olefin was 11% wt, whereas <3% wt is observed in the absence of 1-hexadecene monomer, see Example 1.

GC and NMR data showed the by-products to be mainly methyl-branched alpha olefins having a K-factor of 0.70 ($R^2$=0.99; standard error=0.04 from 6 observations).

Details of the reaction are provided in Table 1.

EXAMPLE 5

Figure 2:
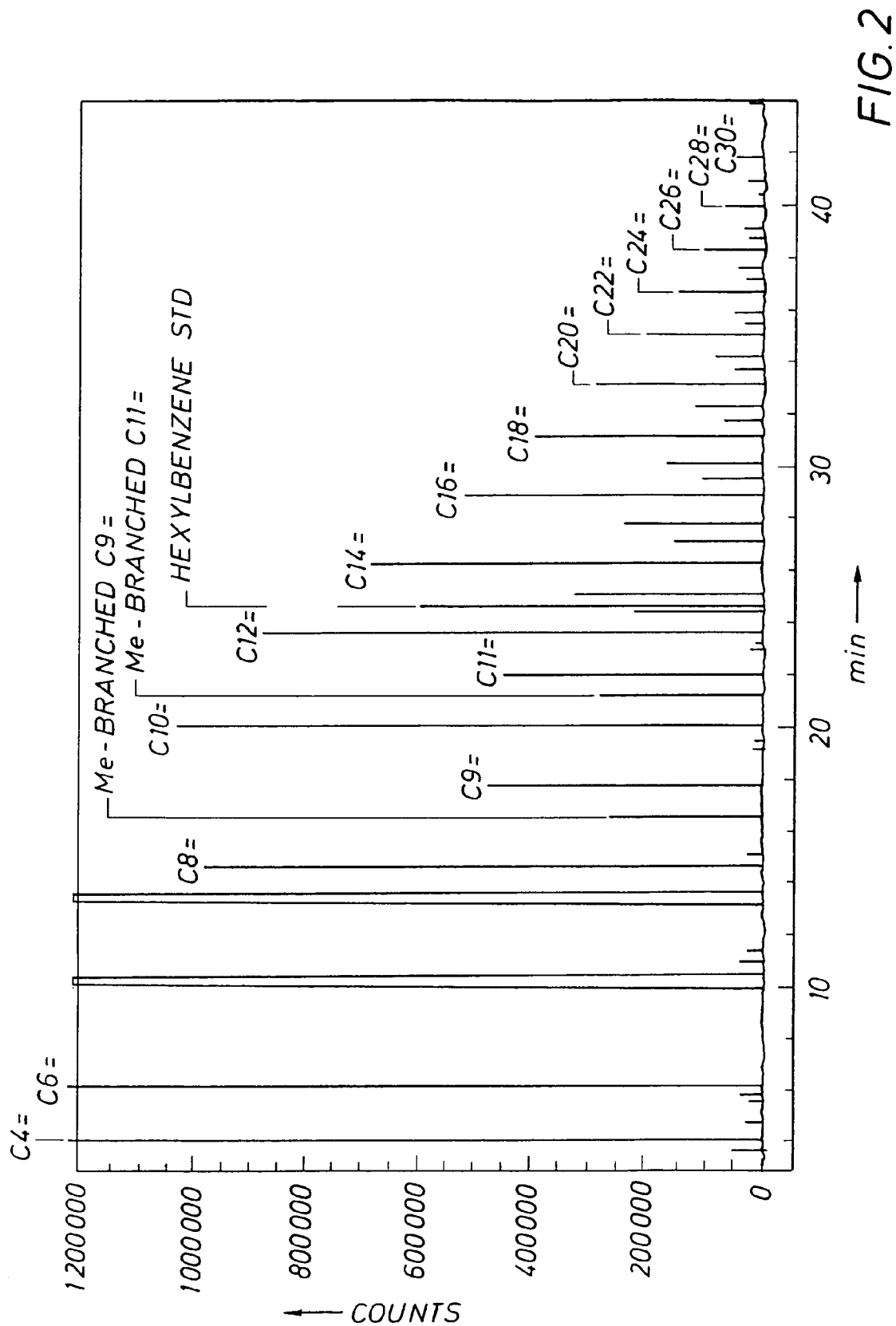
FIG. 2 is a GC-trace of product of Example 5.

Example 5 is a repeat of Example 2, but now at a higher 1-heptene concentration and a lower ethylene pressure of 0.7 MPa illustrating the effect of changing olefin concentrations. Besides even-numbered linear alpha olefins GC analyses showed formation distributions of odd-numbered linear and branched alpha olefins (see FIG. 2 for the GC-trace). The odd ($C_9$-$C_{29}$) linear alpha olefins amounted to 11.9 g, whilst the odd methyl-branched alpha olefins amounted to 6.6 g. The linear $C_{10}$-$C_{28}$ alpha olefins showed a Schulz-Flory distribution, as derived from regression analysis, with a K(even-linear)-factor of 0.64 ($R^2$=1.00; standard error <0.01 for 10 observations). Regression analysis of the odd-numbered linear $C_9$-$C_{29}$ alpha olefins and the odd-numbered-methyl-branched $C_9$-$C_{29}$ alpha olefins gave Schulz-Flory distributions, having a K(odd-linear) of 0.64 ($R^2$=1.00; standard error=0.01 for 11 observations) and a K(odd-branched) of 0.63 ($R^2$=1.00; standard error=0.03 for 11 observations), respectively.

Further details are provided in Table 1.

EXAMPLE 6

Example 6 is a repeat of Example 3, but at different ethylene pressure of 0.7 MPa, demonstrating the effect of changing the olefin concentration. After an ethylene consumption of 68.8 g the reaction was stopped, giving rise to 85.8 g of linear $C_4$-$C_{30}$ alpha olefins and 3.6 g of solids >$C_{30}$. The excess of linear alpha olefin production is attributed to incorporation of starting 1-octene in the final products as shown in Examples 2, 4 and 5.

The linear alpha olefins had a Schulz-Flory distribution with K-factor of 0.70, as derived from regression analysis using the $C_{10}$-$C_{28}$ contents, determined by GC (Regression statistics: $R^2$=1.00; standard error=0.02 from 10 observations).

The T.O.F. was 1.10E+07 mol ethylene/mol Fe*h.

The linear 1-hexene and 1-dodecene purity were 99.2 and 84.7% wt, respectively. GC and NMR data showed the by-products to be mainly methyl-branched alpha olefins having a K-factor of 0.70 ($R^2$=1.00; standard error=0.04 from 10 observations).

Details of the reactions and products are given in Table 1.

EXAMPLE 7

Example 7 is a repeat of Example 6, but at different 1-octene concentration, demonstrating the effect of changing the olefin concentration. The results are similar to those of Example 6. Details of the reactions and products are given in Table 1.

The following series of experiments demonstrate the effects of catalyst systems with different bis-iminepyridine ligands.

EXAMPLE 8

Iron complex X (prepared according to WO-A-99/02472) was employed in a reaction nearly identical to Example 6. The yield of linear alpha olefins in the $C_4$-$C_{30}$ range of was 96.9 g, which is in excess of the ethylene consumption of 68.7 g, which is indicative of 1-octene incorporation in the products.

The linear 1-hexene purity was 98.0% wt and the alkyl-branched 1-dodecene content was 14% wt. GC and NMR data showed the by-products to be mainly methyl- and ethyl-branched (Me- and Et-branched) alpha olefins in a ratio of about 1:1. Details of the reaction are provided in Table 1.

EXAMPLE 9

Iron complex 5 was employed in an 1-octene co-oligomerisation experiment at 0.7 MPa ethylene pressure under conditions similar to that of Example 7. The yield of linear alpha olefins in the $C_4$-$C_{30}$ range of 60.2 g is in excess of the ethylene consumption of 53.5 g.

Figure 3:
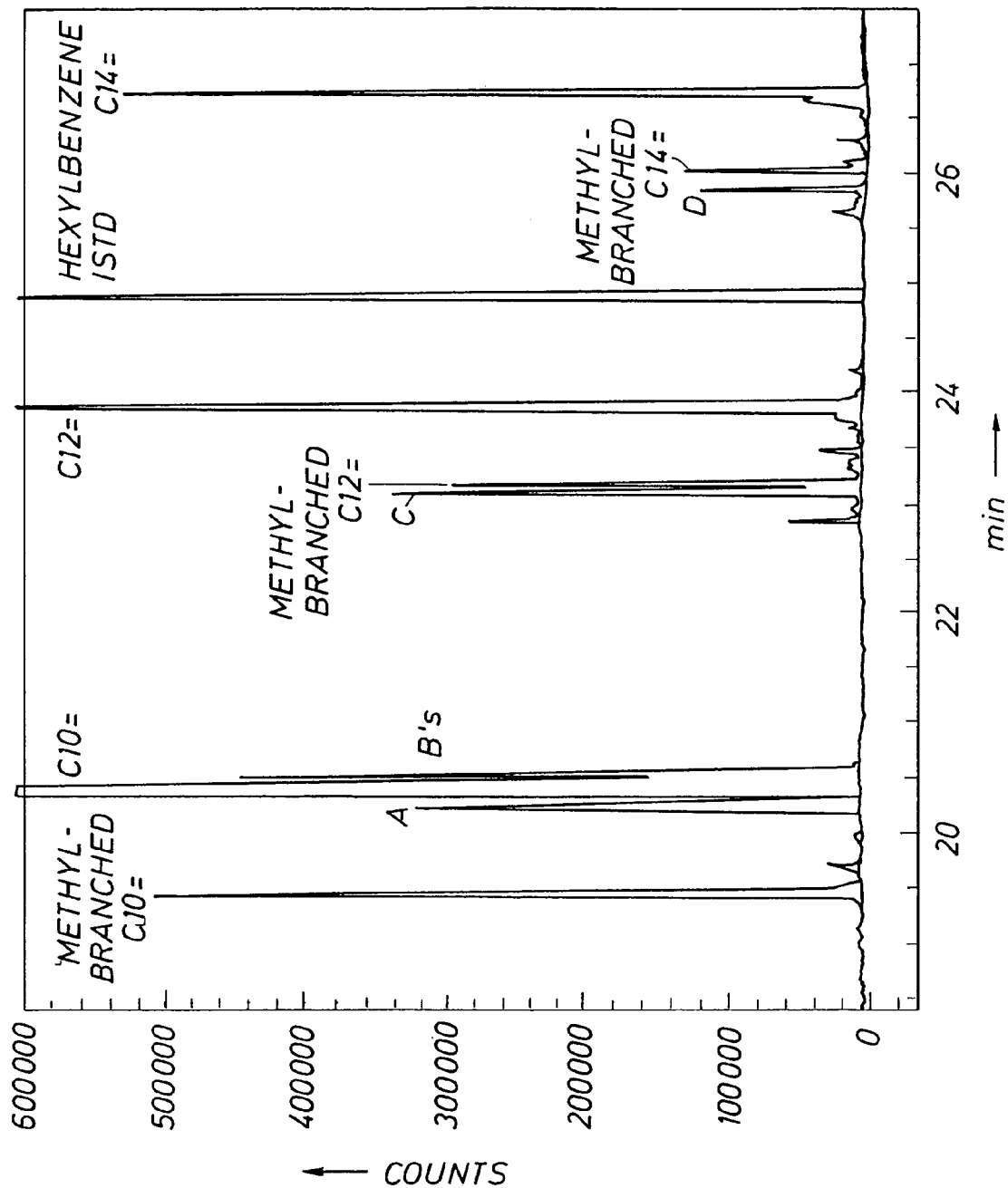
FIG. 3 is a partial gas chromatography (GC) trace of product from Example 9.

The linear 1-hexene purity was 94.7% wt and the alkyl-branched 1-dodecene content was 28% wt. GC and NMR data showed the by-products to be mainly methyl- and ethyl-branched alpha olefins in a ratio of approximately 1:1 (see FIG. 3 for GC-trace wherein A is vinylidene olefin, B is internal olefins, C and D are ethyl branched olefins). Details of the reaction are provided in Table 1.

EXAMPLE 10

Example 10 is a repeat of Example 9, but now using iron complex 5'. The results are similar to those of Example 9. Details are provided in Table 1.

EXAMPLE 11

Iron complex 8 was employed in 1-octene co-oligomerisation experiment almost identical to that of Example 7. The yield of linear alpha olefins in the $C_4$-$C_{30}$ range was 73.6 g which is in excess of the ethylene consumption of 68.6 g.

Linearity of 1-hexene fraction was 96.8% wt and alkyl-branched 1-dodecene content was 20% wt. GC and NMR data showed the by-products to be mainly methyl- and ethyl-branched alpha olefins in a ratio of approximately 1:1. Details of the reaction are provided in Table 1.

EXAMPLE 12

Iron complex 11 was employed in 1-octene co-oligomerisation experiment nearly identical to that of Example 7. The total yield of products was >75.6 g, in excess of ethylene consumption of 68.8 g. The linear 1-hexene purity was 99.2% wt and alkyl-branched 1-dodecene content was 5% wt. GC and NMR data showed the by-products to be mainly methyl-branched alpha olefins. Details of the reaction are provided in Table 1.

EXAMPLE 13

Iron complex 13 was employed in 1-octene co-oligomerisation experiment under conditions similar to that of Example 7. The linear 1-hexene purity was 98.8% wt and the alkyl-branched 1-dodecene content was 4% wt. GC and NMR data showed the by-products to be mainly methyl-branched alpha olefins. Details of the reaction are provided in Table 1.

EXAMPLE 14

Iron complex 15 was employed in 1-octene co-oligomerisation experiment under conditions almost identical to that of Example 6. The linear 1-hexene purity was 99.1% wt and the alkyl-branched 1-dodecene content was 16% wt. GC and NMR data showed the by-products to be mainly methyl-branched alpha olefins. Details of the reaction are provided in Table 1.

EXAMPLE 15

Iron complex 17 was employed in 1-octene co-oligomerisation experiment under conditions almost identical to those of Example 7. The yield of linear alpha olefins in the $C_4$-$C_{30}$ range was 69.5 g which is in excess of the ethylene consumption of 49.8 g. The linear 1-hexene purity was 98.4% wt and the alkyl-branched 1-dodecene content was 17% wt. GC and NMR data showed the by-products to be mainly methyl- and ethyl-branched alpha olefins in a ratio of about 1:1. Details of the reaction are provided in Table 1.

EXAMPLE 16

Iron complex 20 was employed in 1-octene co-oligomerisation experiment under conditions almost identical to those of Example 6. The linear 1-hexene purity was 97.8% wt and the alkyl-branched 1-dodecene content was 21% wt. GC and NMR data showed the by-products to be mainly Me- and Et-branched alpha olefins in a ratio of about 1:1. Details of the reaction are provided in Table 1.

EXAMPLE 17

Iron complex 22 was used in a 1-octene oligomerisation experiment under conditions almost identical to those of Example 6. The K-factor was very low, implying that much of the ethylene is converted into 1-butene, which takes part in the co-oligomerisation. This is reflected by the purity of 1-hexene of 54.4% wt. The remainder are largely branched hexenes. The branched 1-dodecene content was 33% wt. GC indicated the by-products to be mainly Me- and Et-branched alpha olefins in a ratio of about 1:1. Details of the reaction are provided in Table 1.

TABLE 1

| Example Number | Ex. 1 | Ex. 2[1] | Ex. 3 | Ex. 4[2] | Ex. 5[1] | Ex. 6 | Ex. 7 |
|---|---|---|---|---|---|---|---|
| Iron Complex/ (Intake in nmol) | 3 (215) | 3 (518) | 3 (225) | 3 (2166) | 3 (3150) | 3 (198) | 3 (507) |
| [Al]/[Fe] (mol/mol) | 4600 | 2100 | 4400 | 2100 | 650 | 5000 | 2200 |
| Reaction Time (min) | 25 | 23 | 33 | 78 | 40 | 68 | 43 |
| Ethene Pressure (MPa) | 1.6 | 1.6 | 1.6 | 1.6 | 0.7 | 0.7 | 0.7 |

TABLE 1-continued

| | | | | | | | |
|---|---|---|---|---|---|---|---|
| Toluene intake (ml) | 310 | 290 | 60 | 150 | 230 | 60 | 90 |
| 1-Octene intake (ml) | 0 | 34[1] | 260 | 250[2] | 260[1] | 262 | 256 |
| Ethene consumed (g) | 118.2 | 118.3 | 118.0 | 111.5 | 68.8 | 68.8 | 68.7 |
| Linear Product <C32 (g) | 110.6 | 110.3[3] 1.7[4] | 125.4 | 116.3 | 57.6[3] 11.9[4] | 85.8 | 79.7 |
| Branched Product <C32 (g) | n.d. | 1.1[4] | 5.5 | 2.2 | 6.6[4] | 8.7 | 9.3 |
| Isolated Solids >C30 (g) | 2.5 | 2.0 | 9.7 | 7.3 | 0.3 | 3.6 | 2.4 |
| T.O.F. (molC2=/molFe*h) | 4.65E+07 | 2.13E+07 | 3.43E+07 | 1.42E+06 | 1.16E+06 | 1.10E+07 | 6.67E+06 |
| K(linear) | 0.72 | 0.69[3] 0.70[4] | 0.73 | 0.72 | 0.64[3] 0.64[4] | 0.70 | 0.69 |
| Lin.1-$C_6$= purity (% wt) | 99.5 | 99.0 | 99.5 | 99.6 | 99.0 | 99.2 | 99.1 |
| Lin.1-$C_{12}$= purity (% wt) | 97.7 | 96.1 | 91.9 | 97.9 | 98.0 | 84.7 | 83.3 |
| K(branch) | n.d. | 0.68 | 0.71 | 0.70 | 0.63 | 0.70 | 0.70 |
| Branched 1-$C_{12}$= (% wt) | <2 | 40[6] | 7 | 11[5] | 38[6] | 14 | 15 |

| Example Number | Ex. 8[7] | Ex. 9 | Ex. 10 | Ex. 11 | Ex. 12 | Ex. 13 | Ex. 14 |
|---|---|---|---|---|---|---|---|
| Iron Complex/ (Intake in nmol) | X[7] (562) | 5 (1920) | 5' (1780) | 8 (3510) | 11 (2540) | 13 (3170) | 15 (672) |
| [Al]/[Fe] (mol/mol) | 1900 | 900 | 900 | 600 | 700 | 600 | 1700 |
| Reaction Time (min) | 18 | 69 | 74 | 59 | 58 | 62 | 20 |
| Ethene Pressure (MPa) | 0.7 | 0.7 | 0.7 | 0.7 | 0.7 | 0.7 | 0.7 |
| Toluene intake (ml) | 60 | 120 | 90 | 90 | 90 | 150 | 60 |
| 1-Octene intake (ml) | 247 | 243 | 230 | 254 | 242 | 261 | 260 |
| Ethene consumed (g) | 68.7 | 53.5 | 80.4 | 68.6 | 68.8 | 33.6 | 68.4 |
| Linear Product <C32 (g) | 96.9 | 60.2 | 91.5 | 73.6 | 55.1 | 29.1 | 49.4 |
| Isolated Solids >C30 (g) | 5.9 | <0.1 | <0.1 | 7.6 | 20.5 | 11.7 | 9.0 |
| T.O.F. (molC2=/molFe*h) | 1.44E+07 | 8.70E+05 | 1.31E+06 | 7.12E+05 | 1.00E+06 | 3.66E+05 | 1.11E+07 |
| K(linear) | 0.70 | 0.46 | 0.44 | 0.73 | 0.82 | 0.82 | 0.76 |
| Lin.1-$C_6$= purity (% wt) | 98.0 | 94.7 | 92.5 | 96.8 | 99.2 | 98.8 | 99.1 |
| Lin.1-$C_{12}$= purity (% wt) | 82.0 | 66.3 | 65.5 | 75.9 | 94.3 | 94.9 | 82.6 |
| Branched 1-$C_{12}$= (% wt) | 14 | 28 | 29 | 20 | 5 | 4 | 16 |

| Example Number | Ex. 15 | Ex. 16 | Ex. 17 |
|---|---|---|---|
| Iron Complex/ (Intake in nmol) | 17 (353) | 20 (984) | 22 (4230) |

TABLE 1-continued

|  | | | |
|---|---|---|---|
| [Al]/[Fe] (mol/mol) | 2900 | 1300 | 600 |
| Reaction Time (min) | 42 | 59 | 45 |
| Ethene Pressure (MPa) | 0.7 | 0.7 | 0.7 |
| Toluene intake (ml) | 90 | 60 | 60 |
| 1-Octene intake (ml) | 255 | 234 | 237 |
| Ethene consumed (g) | 49.8 | 42.2 | 64.8 |
| Linear Product <C32 (g) | 69.5 | 65.0 | 30.8 |
| Isolated Solids >C30 (g) | 2.1 | 1.5 | <0.1 |
| T.O.F. (molC2=/molFe*h) | 7.19 E+06 | 1.54E+06 | 5.47E+05 |
| K(linear) | 0.66 | 0.59 | 0.2 |
| Lin.1-$C_6$= purity (% wt) | 98.5 | 97.8 | 54.4 |
| Lin.1-$C_{12}$= purity (% wt) | 79.4 | 75.2 | 61.1 |
| Branched 1-$C_{12}$= (% wt) | 17 | 21 | 33 |

Experiments carried out at 70° C. in 1-octene/toluene, using 1-litre steel autoclave, unless indicated otherwise.
n.d. = not determined.
[1] 1-Heptene used instead of 1-octene.
[2] 1-Hexadecene used instead of 1-octene.
[3] Refers to even-numbered alpha olefins.
[4] Refers to odd-numbered alpha olefins.
[5] Weight ratio of alkyl-branched 1-$C_{20}$= over alkyl-branched and linear 1-$C_{20}$=, in % wt.
[6] Weight ratio of alkyl-branched 1-$C_{11}$= over alkyl-branched and linear 1-$C_{11}$=, in % wt.
[7] Catalyst prepared according to WO-A-99/02472.

We claim:

1. An olefin composition comprising linear alpha olefins and alkyl-branched alpha olefins, wherein said composition contains greater than 5% wt. alkyl-branched alpha olefins based on the total weight of linear alpha olefins and alkyl-branched alpha olefins in the product composition, wherein the alkyl branched alpha olefins have a general structure:

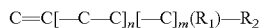

C=C[—C—C]$_n$[—C]$_m$($R_1$)—$R_2$ wherein $R_1$ is a methyl group or an ethyl group; n=1 or 2; m=1; and $R_2$ is an optionally substituted hydrocarbyl containing 1 to 30 carbon atoms.

2. The composition of claim 1 wherein said alkyl-branched alpha olefins are methyl- and/or ethyl branched alpha olefins.

3. The composition of claim 1 wherein the alkyl-branched olefins comprise greater than 10% by weight based on the total weight of linear alpha olefins and alkyl-branched alpha olefins in the product composition.

4. The composition of claim 3 wherein the alkyl-branched olefins comprise greater than 15% by weight based on the total weight of linear alpha olefins and alkyl-branched alpha olefins in the product composition.

5. The composition of claim 4 wherein the alkyl-branched olefins comprise greater than 25% by weight based on the total weight of linear alpha olefins and alkyl-branched alpha olefins in the product composition.

6. The composition of claim 1 wherein $R_2$ is an ethyl group.

7. The composition of claim 1 wherein $R_2$ is a methyl group.

8. An olefin composition comprising linear alpha olefins and alkyl-branched alpha olefins, wherein said composition contains greater than 5% wt. alkyl-branched alpha olefins based on the total weight of linear alpha olefins and alkyl-branched alpha olefins in the product composition wherein said composition is made from a process comprising:

co-oligomerising one or more alpha olefins other than ethylene with ethylene in the presence of a metal catalyst system employing one or more bis-aryliminepyridine MX$_a$ complexes and/or one or more [bis-aryliminepyridine MY$_p$.L$_b^+$][NC$^-$]$_q$ complexes, said bis-aryliminepyridine complexes comprising a ligand of the formula,

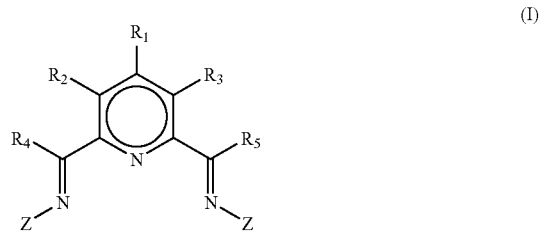

(I)

wherein M is a metal atom selected from Fe or Co; a is 2 or 3; X is halide, optionally substituted hydrocarbyl, alkoxide, amide, or hydride; Y is a ligand which may insert an olefin; NC— is a non-coordinating anion; p+q is 2 or 3, matching the formal oxidation of said metal atom; L is a neutral Lewis donor molecule; b=0, 1, or 2; $R_1$-$R_5$ are each, independently, hydrogen, optionally substituted hydrocarbyl, an inert functional group, or any two of $R_1$-$R_3$ vicinal to one another taken together may form a ring; each Z, which may be identical or different, is an optionally substituted aromatic hydrocarbon ring; an optionally substituted polyaromatic hydrocarbon moiety; an optionally substituted heterohydrocarbyl moiety; or an optionally substituted aromatic hydrocarbon ring in combination with a metal, said optionally substituted aromatic hydrocarbon ring being π-co-ordinated to the metal; said co-oligomerising being carried out under conditions comprising an ethylene pressure of from about 0.1 MPa to about 1.6 MPa and a temperature of from about −100° C. to about 300° C.

9. The composition of claim 8 wherein said alkyl-branched alpha olefins are methyl- and/or ethyl branched alpha olefins.

10. The composition of claim 8 wherein the alkyl-branched alpha olefins have the general structure:

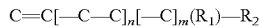
C=C[—C—C]$_n$[—C]$_m$($R_1$)—$R_2$ wherein $R_1$ is a methyl group; n=0, 1, 2; m=1; and $R_2$ is an optionally substituted hydrocarbyl.

11. The composition of claim 8 wherein the alkyl-branched alpha olefin has the general structure:

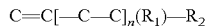
C=C[—C—C]$_n$($R_1$)—$R_2$ wherein $R_1$ is an ethyl group; n=0, 1, 2; and $R_2$ is an optionally substituted hydrocarbyl.

12. An olefin composition comprising linear alpha olefins and alkyl-branched alpha olefins, wherein said composition contains greater than 5% wt. alkyl-branched alpha olefins based on the total weight of linear alpha olefins and alkyl-branched alpha olefins in the product composition wherein said composition is made from a process comprising:

co-oligomerising one or more alpha olefins other than ethylene with ethylene in the presence of a metal catalyst system employing one or more bis-aryliminepyridine MX$_a$ complexes and/or one or more [bis-aryliminepyridine MY$_p$.L$_b^+$][NC$^-_q$ complexes, said bis-aryliminepyridine complexes comprising a ligand of the formula,

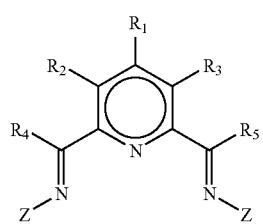

(I)

wherein M is a metal atom selected from Fe or Co; a is 2 or 3; X is halide, optionally substituted hydrocarbyl, alkoxide, amide, or hydride; Y is a ligand which may insert an olefin; NC$^-$ is a non-coordinating anion; p+q is 2 or 3, matching the formal oxidation of said metal atom; L is a neutral Lewis donor molecule; b=0, 1, or 2; $R_1$-$R_5$ are each, independently, hydrogen, optionally substituted hydrocarbyl, an inert functional group, or any two of $R_1$-$R_3$ vicinal to one another taken together may form a ring; each Z, which may be identical or different, is an optionally substituted aromatic hydrocarbon ring; an optionally substituted polyaromatic hydrocarbon moiety; an optionally substituted heterohydrocarbyl moiety; or an optionally substituted aromatic hydrocarbon ring in combination with a metal, said optionally substituted aromatic hydrocarbon ring being π-co-ordinated to the metal; said co-oligomerizing being carried out under conditions comprising an ethylene pressure of from about 0.1 MPa to about 1.6 MPa and a temperature of about −100° C. to about 300° C., wherein alpha olefin co-monomer is present in a concentration of greater than 1 mol.l$^{-1}$.

13. The composition of claim 12 wherein said alkyl-branched alpha olefins are methyl- and/or ethyl branched alpha olefins.

14. The composition of claim 12 wherein the alkyl-branched alpha olefins have the general structure:

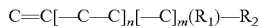
C=C[—C—C]$_n$[—C]$_m$($R_1$)—$R_2$ wherein $R_1$ is a methyl group; n=0, 1, 2; m=1; and $R_2$ is an optionally substituted hydrocarbyl.

15. The composition of claim 12 wherein the alkyl-branched alpha olefin has the general structure:

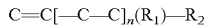
C=C[—C—C]$_n$($R_1$)—$R_2$ wherein $R_1$ is an ethyl group; n=0, 1, 2; and $R_2$ is an optionally substituted hydrocarbyl.

16. The olefin composition of claim 1 wherein the linear alpha olefins may contain from 4 to 30 carbon atoms and the alkyl-branched alpha olefins may contain from 4 to 30 carbon atoms.

17. The olefin composition of claim 16 wherein the linear alpha olefins contain from 4 to 20 carbon atoms and the alkyl-branched alpha olefin contain from 4 to 20 carbon atoms.

18. The olefin composition of claim 17 wherein the alkyl-branched alpha olefin comprise $C_8$-$C_{16}$ methyl-branched alpha olefins.

19. The olefin composition of claim 8 wherein the linear alpha olefins may contain from 4 to 30 carbon atoms and the alkyl-branched alpha olefins may contain from 4 to 30 carbon atoms.

20. The olefin composition of claim 19 wherein the linear alpha olefins contain from 4 to 20 carbon atoms and the alkyl-branched alpha olefin contain from 4 to 20 carbon atoms.

21. The olefin composition of claim 20 wherein the alkyl-branched alpha olefin comprise $C_{8-C16}$ methyl-branched alpha olefins.

22. The olefin composition of claim 12 wherein the linear alpha olefins may contain from 4 to 30 carbon atoms and the alkyl-branched alpha olefins may contain from 4 to 30 carbon atoms.

23. The olefin composition of claim 22 wherein the linear alpha olefins contain from 4 to 20 carbon atoms and the alkyl-branched alpha olefin contain from 4 to 20 carbon atoms.

24. The olefin composition of claim 23 wherein the alkyl-branched alpha olefin comprise $C_8$-$C_{16}$ methyl-branched alpha olefins.

* * * * *